United States Patent
Dariush

(10) Patent No.: US 7,469,166 B2
(45) Date of Patent: Dec. 23, 2008

(54) SYSTEM AND METHOD OF PREDICTING NOVEL MOTION IN A SERIAL CHAIN SYSTEM

(75) Inventor: Behzad Dariush, Sunnyvale, CA (US)

(73) Assignee: Honda Motor Co., Ltd., Tokyo (JP)

( * ) Notice: Subject to any disclaimer, the term of this patent is extended or adjusted under 35 U.S.C. 154(b) by 838 days.

(21) Appl. No.: 11/038,691

(22) Filed: Jan. 19, 2005

(65) Prior Publication Data
US 2005/0209534 A1 Sep. 22, 2005

Related U.S. Application Data

(63) Continuation-in-part of application No. 10/151,647, filed on May 16, 2002, now Pat. No. 7,135,003.

(60) Provisional application No. 60/353,378, filed on Jan. 31, 2002, provisional application No. 60/301,891, filed on Jun. 29, 2001.

(51) Int. Cl.
*G06F 19/00* (2006.01)

(52) U.S. Cl. ............... 700/245; 700/189; 700/190; 700/217; 700/254; 700/258; 700/259; 700/260; 700/261; 700/262; 318/568.1; 701/23; 901/15; 901/16; 901/21; 901/39

(58) Field of Classification Search ............... 700/245, 700/213, 249, 258, 260, 261, 264, 254, 218, 700/259, 262; 414/331.03, 331.04, 5, 591, 414/6; 901/3, 9; 318/628, 632
See application file for complete search history.

(56) References Cited

U.S. PATENT DOCUMENTS

| 4,244,120 A | 1/1981 | Harris |
|---|---|---|
| 4,786,847 A | 11/1988 | Daggett et al. |
| 4,834,200 A | 5/1989 | Kajita |
| 5,044,360 A | 9/1991 | Janke |
| 5,136,227 A | 8/1992 | Nakano et al. |
| 5,203,346 A | 4/1993 | Fuhr et al. |
| 5,247,432 A | 9/1993 | Ueda |
| 5,323,549 A | 6/1994 | Segel et al. |
| 5,362,288 A | 11/1994 | Razon |
| 5,432,417 A | 7/1995 | Takenaka et al. |
| 5,459,659 A | 10/1995 | Takenaka |
| 5,570,286 A | 10/1996 | Margolis et al. |
| 5,625,577 A | 4/1997 | Kunii et al. |

(Continued)

FOREIGN PATENT DOCUMENTS

| JP | 2000-249570 | 9/2000 |
|---|---|---|
| RU | 2 107 328 C1 | 3/1998 |
| WO | WO 00/35346 | 6/2000 |
| WO | WO 03/002054 | 1/2003 |

OTHER PUBLICATIONS

PCT International Search Report and Written Opinion, PCT/US06/14069, Aug. 31, 2007, 8 pages.

(Continued)

*Primary Examiner*—Khoi H. Tran
*Assistant Examiner*—McDieunel Marc
(74) *Attorney, Agent, or Firm*—Fenwick & West LLP; Mark Duell

(57) ABSTRACT

A method of predicting kinematic data for a segment. The method comprises the steps of determining a modified acceleration using at least original kinematic data, estimating a joint load for a joint of the segment by using at least the modified acceleration, and predicting kinematic data for the segment based on one or more modified parameters. Therefore, various embodiments advantageously allow for prediction of novel motion.

18 Claims, 13 Drawing Sheets

U.S. PATENT DOCUMENTS

| | | | |
|---|---|---|---|
| 5,659,480 | A | 8/1997 | Anderson et al. |
| 5,706,589 | A | 1/1998 | Marc |
| 5,808,433 | A | 9/1998 | Tagami et al. |
| 5,835,693 | A | 11/1998 | Lynch et al. |
| 5,942,869 | A | 8/1999 | Katou et al. |
| 5,982,389 | A | 11/1999 | Guenter et al. |
| 6,045,524 | A | 4/2000 | Hayashi et al. |
| 6,076,025 | A | 6/2000 | Ueno |
| 6,152,890 | A | 11/2000 | Kupfer et al. |
| 6,161,080 | A | 12/2000 | Aouni-Ateshian et al. |
| 6,289,265 | B1 | 9/2001 | Takenaka et al. |
| 6,445,983 | B1 | 9/2002 | Dickson et al. |
| 6,505,096 | B2 | 1/2003 | Takenaka et al. |
| 6,580,969 | B1 | 6/2003 | Ishida et al. |
| 6,633,783 | B1 | 10/2003 | Dariush et al. |
| 6,640,160 | B2 | 10/2003 | Takahashi et al. |
| 6,750,866 | B1 | 6/2004 | Anderson |
| 6,766,204 | B2 | 7/2004 | Niemeyer et al. |
| 6,785,591 | B1 | 8/2004 | Hansson |
| 6,915,150 | B2 * | 7/2005 | Cinquin et al. ............. 600/407 |
| 6,943,520 | B2 | 9/2005 | Furuta et al. |
| 7,010,390 | B2 | 3/2006 | Graf et al. |
| 7,013,201 | B2 | 3/2006 | Hattori et al. |
| 7,024,279 | B2 | 4/2006 | Rose, III et al. |
| 7,112,938 | B2 | 9/2006 | Takenaka et al. |
| 7,135,003 | B2 | 11/2006 | Dariush |
| 7,184,858 | B2 | 2/2007 | Okazaki et al. |
| 7,191,036 | B2 | 3/2007 | Takenaka et al. |
| 7,217,247 | B2 * | 5/2007 | Dariush et al. ................. 601/5 |
| 7,260,450 | B2 | 8/2007 | Okazaki et al. |
| 7,333,111 | B2 * | 2/2008 | Ng-Thow-Hing et al. ... 345/473 |
| 2003/0018283 | A1 | 1/2003 | Dariush |
| 2003/0023415 | A1 | 1/2003 | Nakamura et al. |
| 2003/0115031 | A1 * | 6/2003 | Dariush et al. ................ 703/11 |
| 2004/0031169 | A1 | 2/2004 | Jensen et al. |
| 2004/0102723 | A1 | 5/2004 | Horst |
| 2004/0107780 | A1 | 6/2004 | Kawai et al. |
| 2004/0158175 | A1 | 8/2004 | Ikeuchi et al. |
| 2004/0193318 | A1 | 9/2004 | Ito |
| 2004/0249319 | A1 | 12/2004 | Dariush |
| 2004/0254771 | A1 | 12/2004 | Riener et al. |
| 2005/0070834 | A1 | 3/2005 | Herr et al. |
| 2005/0102111 | A1 | 5/2005 | Dariush et al. |
| 2005/0104548 | A1 | 5/2005 | Takenaka et al. |
| 2005/0209535 | A1 * | 9/2005 | Dariush ..................... 600/595 |
| 2006/0046909 | A1 | 3/2006 | Rastegar et al. |
| 2006/0100818 | A1 | 5/2006 | Nakamura et al. |
| 2006/0139355 | A1 | 6/2006 | Tak et al. |

OTHER PUBLICATIONS

PCT International Search Report and Written Opinion, PCT/US06/01343, Aug. 15, 2007, 8 pages.

F. Akhlaghi and M.G. Pepper, "In-shoe Biaxial Shear Force Measurement: the Kent Shear System," Medical & Biological Engineering & Computing, Jul. 1996, vol. 34, pp. 315-317.

R. Anderssen and P. Bloomfield, "Numerical Differentiation Procedures for Non-Exact Data," Numererische Mathematik, 1974, vol. 22, pp. 157-182.

H.R. Busby and D.M. Trujillo, "Numerical Experiments With a New Differentiation Filter," Transactions of the ASME—Journal of Biomechanical Engineering, Nov. 1985, vol. 107, pp. 293-299.

E. Y. Chao and K. Rim, "Application of Optimization Principles in Determining the Applied Moments in Human Leg Joints During Gait," J. Biomechanics, 1973, vol. 6, pp. 497-510, Pergamon Press, Great Britain.

J. J. Craig, "Nonlinear Control of Manipulators," Introduction to Robotics Mechanics and Control, 2nd, Ed., 1989, Chapter 10, pp. 333-361.

J. Cullum, "Numerical Differentiation and Regularization," Siam J. Numer. Anal., Jun. 1971, vol. 8, No. 2, pp. 254-265.

B. Dariush, H. Hemami, and M. Parnianpour, "Multi-Modal Analysis of Human Motion From External Measurements,", Transactions of the ASME, Jun. 2001, vol. 123, pp. 272-278.

B. Dariush, H. Hemami, and M. Parnianpour, "A Well-Posed, Embedded Constraint Representation of Joint Moments From Kinesiological Measurements," Journal of Biomechanical Engineering, Aug. 2000, vol. 122, pp. 437-445.

C.R. Dohrmann, H.R. Busby, and D.M. Trujillo, "Smoothing Noisy Data Using Dynamic Programming and Generalized Cross-Validation" Transactions of the ASME—Journal of Biomechanical Engineering, Feb. 1988, vol. 110, pp. 37-41.

G. Giakas and V. Baltzopoulos, "A Comparison of Automatic Filtering Techniques Applied to Biomechanical Walking Data," J. Biomechanics, 1997, vol. 00, No. 00, 4 pages.

G. Giakas and V. Baltzopoulos, "Optimal Digital Filtering Requires a Different Cut-Off Frequency Strategy for the Determination of the Higher Derivatives," J. Biomechanics, Apr. 1997, vol. 28, No. 00, 5 pages.

H. Hatze, "The Use of Optimally Regularized Fourier Series for Estimating Higher-Order Derivatives of Noisy Biomechanical Data," J. Biomechanics, 1981, vol. 14, pp. 13-18.

R. Hosein and M. Lord, "A Study of In-shoe Plantar Shear in Normals," Clinical Biomechanics, 2000, vol. 15, pp. 46-53.

C.F. Runge et al., "Estimating Net Joint Torques From Kinesiological Data Using Optimal Linear System Theory." IEEE Transactions on Biomedical Engineering, Dec. 1995, vol. 42, No. 12, pp. 1158-1164.

W. Simons and K. H. Yang, "Differentiation of Human Motion Data Using Combined Spline and Least Squares Concepts," Journal of Biomechanical Engineering, Transactions of the ASME, Aug. 1991, vol. 113, pp. 348-151.

D.A. Winter, "Kinetics: Forces and Moments of Force," Biomechanics and Motor Control of Human Movement, 2nd Ed., New York, 1990, Chapter 4.

H.J. Woltring, "A Fortran Package for Generalized, Cross Validatory Spline Smoothing and Differentiation," Adv. Eng. Software, 1986, vol. 8, No. 2, pp. 104-107.

H. J. Woltring, "On Optimal Smoothing and Derivative Estimation From Noisy Displacement Data in Biomechanics," Human Movement Science, vol. 4, 1985, pp. 229-245.

Anderson, F and Pandy, M., "Static And Dynamic Optimization Solutions For Gait Are Practically Equivalent," *Journal of Biomechanics*, 34, 2001, pp. 153-161.

Anderson, F. and Pandy, M., "Dynamic Optimization of Human Walking," *Journal of Biomechanical Engineering*, Oct. 2001, vol. 123, pp. 381-390.

Baruh, H., Analytical *Dynamics*, Chapter 7, Rigid Body Kinematics, McGraw-Hill, 1999, pp. 355-371.

Crowninshield, R. D. and Brand, R. A., "A Physiologically Based Criterion Of Muscle Force Prediction In Locomotion," *Journal of Biomechanics*, vol. 14, No. 11, 1981, pp. 793-801.

Dariush, B., "A Novel Algorithm For Generating A Forward Dynamics Solution To The Traditional Inverse Dynamics Problem," In *4th World Congress of Biomechanics*, Calgary, Canada, 2002.

Dariush, B., "A Forward Dynamics Solutions To Multi-Modal Inverse Dynamics Problems," In *International Society of Biomechanics, XIXth Congress*, Dunedin, NZ, 2003.

Delp, S. and Loan, J. P., "A Computational Framework for Stimulating and Analyzing Human and Animal Movement," *IEEE Computing in Science and Engineering*; vol. 2, No. 5, 2000, pp. 46-55.

Grood, E.S. and Suntay, W.J., "A Joint Coordinate System For The Clinical Description Of Three-Dimensional Motions: Application To The Knee," *Journal of Biomechanical Engineering*, vol. 105, 1983, pp. 136-144.

Hemami, H. and Wyman, B., "Modeling And Control Of Constrained Dynamic Systems With Application To Biped Locomotion In The Frontal Plane," *IEEE Transactions on Automatic Control*, vol. 4, No. 4, Aug. 1979, pp. 526-535.

Hemami, H., "A State Space Model For Interconnected Rigid Bodies," *IEEE Trans. on Automatic Control*, vol. 27, No. 2, Apr. 1982, pp. 376-382.

Jalics, L. et al., "A Control Strategy For Terrain Adaptive Bipedal Locomotion*," *Autonomous Robots*, 4, 1997, pp. 243-257.

Kawato, M., "Internal Models For Motor Control And Trajectory Planning," Current Opinion in Neurobiology, 1999, 9, pp. 718-727.

Khatib, O., A Unified Approach For Motion And Force Control Of Robot Manipulators: The Operational Space Formulation, IEEE Journal of Robotics and Automation, RA-3(1), 1987, pp. 43-53.

Klein, C. A. et al., Review Of Pseudoinverse Control For Use With Kinematically Redundant Manipulators, IEEE Transactions on Systems, Man, and Cybernetics, vol. 13, No. 2, 1983, pp. 245-250.

Piazza, S. and Delp, S., "Three-Dimensional Dynamic Simulation of Total Knee Replacement Motion During a Step-up Task," Journal of Biomechanical Engineering, vol. 123, 2001, pp. 599-606.

Thelen, D. et al., "Generating Dynamic Simulations of Movement Using Computed Muscle Control," Journal of Biomechanics, 36, 2003, pp. 321-328.

Vaughan, C. L. et al., "Appendix B., Detailed Mathematics Used in GaitLab," Dynamics of Human Gait, Second Edition, Kiboho Publishers, Cape Town South Africa, 1999, pp. 83-106.

Vukobratovic, M. et al., Scientific Fundamentals of Robotics 7: Biped Locomotion. Springer-Verlag, 1990, pp. 17-27.

Wittenburg, J., Dynamics of Systems of Rigid Bodies, B.G. Teubner Stuttgart, 1977, pp. 29-30.

Agarwal, S.K. et al., "Theory and Design of an Orthotic Device for Full or Partial Gravity-Balancing of a Human Leg During Motion," IEEE Transactions on Neural Systems and Rehabilitation Engineering, Jun. 2004, vol. 12, No. 2.

Atkeson, C.G., "Learning Arm Kinematics and Dynamics", Annual Reviews, Inc., 1989, vol. 12, pp. 157-183.

Blaya, J., "Force-Controllable Ankle Foot Orthosis (AFO) to Assist Drop Foot Gait," Feb. 2003, web.mit.edu/jblaya/www/MSthesis_final.pdf.

Bronzino, J.D., et al. "The Biomedical Engineering Handbook", IEEE Press, 2nd Ed. vol. 2, 2000, Chapter 142, pp. 1-17.

Flanagan, R.J., et al., "The Role of Internal Models in Motion Planning and Control: Evidence from Grip Force Adjustments During Movements of Hand-Held Loads", The Journal of Neuroscience, Feb. 15, 1997, vol. 17(4), pp. 1519-1528.

Gagnon, D. et al., "The Influence of Dynamic Factors on Triaxial Net Muscular Moments at the L5/S1 Joint During Asymmetrical Lifting and Lowering", Journal of Biomechanics, vol. 25, pp. 891-901, 1992.

Gagnon, M. et al., "Muscular Mechanical Energy Expenditure as Process for Detecting Potential Risks in Manual Materials Handling," J. Biomech., Nov. 1991, pp. 191-203, vol. 24, No. 3/4.

Gruber, K., et al., "A Comparative Study of Impace Dynamics: Wobbling Mass Model Versus Rigid Body Models", Journal of Biomechanics, 31 (1998), pp. 439-444.

Hayashibara, Y. et al., "Design of a Power Assist System with Consideration of Actuator's Maximum Torque," 4th IEEE International Workshop on Robot and Human Communication, RO-MAN'95, Tokyo, Jul. 5-7, 1995, pp. 379-384, [online] Retrieved from the Internet<URL:http://ieeexplore.ieee.org/xpl/abs_free.jsp?arNumber=531990>.

Hemami, H., "A Feedback On-Off Model of Biped Dynamics", IEEE Transactions on Systems, Man, and Cybernetics, Jul. 1980, vol. SMC-10, No. 7, pp. 376-383.

Hsiang, S.H. et al., "Three Different Lifting Strategies for Controlling the Motion Patterns of the External Load", Ergonomics, vol. 40, pp. 928-939, 1997.

Jezernk, S. et al., "Robotic Orthosis Lokomat: A Rehabilitation and Research Tool," Neuromodulation, 2003, pp. 108-115, vol. 6, No. 2.

Kato, H. et al., "The Concept of a Walking Assistance Suit", The Japanese Society of Mechanical Engineers, Aug. 2001.

Kawato, M., "Adapation and Learning in Control of Voluntary Movement by the Central Nervous System", 1989, Advanced Robotics, vol. 3, pp. 229-249.

Kawato, M., et al., "The Cerebellum and VOR/OKR Learning Models", Elsevier Science Publishers Ltd., 1992, vol. 15, No. 11, pp. 445-453.

Park, J.H. et al., Biped Robot Walking Using Gravity-Compensated Inverted Pendulum Mode and Computed Torque Control, 1998 IEEE Conference on Robotics and Automation, May 16-20, 1998, pp. 2528-2533, vol. 4, [online] Retrieved from the Internet<URL:http://ieeexplore.ieee.org/xpl/abs_free.jsp?arNumber=680985>.

Rahman, T. et al., "A Simple Technique to Passively Gravity-Balance Articulated Mechanisms," Journal of Mechanical Design, 1995, pp. 655-658, vol. 117, No. 4.

Shadmehr, R. et al., "Interference in Learning Internal Models of Inverse Dynamics in Humans," Advances in Neural Information Processing Systems, 1995, pp. 1117-1224, Chapter 7.

Shadmehr, R., "Learning Virtual Equilibrium Trajectories for Control of a Robot Arm", Neural Computation, 1990, vol. 2, pp. 436-446.

Transmittal of the International Search Report, PCT/US02/20829, Dec. 12, 2002, 4 pages.

Wells, R. et al., "Internal and Physiological Responses During Concentric and Eccentric Cycle Ergometry," Eur. J. Appl. Physiol., 1986, pp. 291-301, vol. 55.

Wolpert, D.M., et al., "Ocular Limit Cycles Induced by Delayed Retinal Feedback", Experimental Brain Research, 1993, vol. 96, pp. 173-180.

Written Opinion, PCT/IB02/04311, Feb. 20, 2003, 2 pages.

Zajac, F.E., "Muscle and Tendon Properties, Models, Scaling, and Application to Biomechancis and Motor Control", 1989, vol. 17, Issue 4, pp. 359-411.

Wyeth, G. F., et al., "Distributed Digital Control of a Robot Arm," Proceedings of the Australian Conference on Robotics and Automation (ACRA 2000), Aug. 30-Sep. 1, 2000, pp. 217-222, [online] [retrieved on Dec. 31, 2006] Retrieved from the Internet: <URL: www.itee.uq.edu.au/~wyeth/Publications/puma.PDF>.

PCT International Search Report and Written Opinion, PCT/US06/22582, Feb. 2, 2007, 8 pages.

PCT International Search Report and Written Opinion, PCT/US05/11908, Mar. 8, 2007, 7 pages.

Burdea, G. et al., "Virtual Reality Technology", 1994, pp. 33-37, John Wiley and Sons, Inc.

"Berkeley Researchers Developing Robotic Exoskeleton That Can Enhance Human Strength and Endurance,"ScienceDaily LLC, 1995-2004, [online] [Retrieved on Oct. 9, 2006] Retrieved from the Internet<URL:http://bleex.me.berkeley.edu/bleexhistPDFs/sciencedaily.pdf>.

Durfee, W.K., "Preliminary Design and Simulation of a Pneumatic, Stored-Energy, Hybrid Orthosis for Gait Restoration," Proceedings of IMECE04, 2004 ASME International Mechanical Engineering Congress, Nov. 13-20, 2004, [online] [Retrieved on Oct. 9, 2006] Retrieved from the Internet<URL:http://www.me.umn.edu/~wkdurfee/publications/IMECE2004-60075.pdf>.

International Search Report and Written Opinion, PCT/US06/11727, Nov. 9, 2006, 9 pages.

Isaacs, P.M. et al., "Controlled Dynamic Simulation with Kinematic Constraints, Behavior Functions, and Inverse Dynamics," Computer Graphics, Jul. 1987, pp. 215-224, vol. 21, No. 4.

Madigan, R.R., "Ankle-Foot Orthoses (AFO's) in Spastic Cerebral Palsy," Fillauer LLC, [online] [Retrieved on Oct. 9, 2006] Retrieved from the Internet<URL:http://www.fillauer.com/education/ED_afo.html#dynamic>.

Pratt, G.A. et al., "Active Orthotics for Helping the Neuromuscularly Impaired to Walk," [online] [Retrieved on Oct. 9, 2006] Retrieved from the Internet<URL:http://www.vcl.uh.edu/~rcv03/materials/grant/9733740.1064791086.pdf>.

"Regenerative Foot Braking," [online] [Retrieved on Oct. 9, 2006] Retrieved from the Internet<URL:http://www.halfbakery.com/idea/regenerative_20foot_20braking#1069693200>.

"Sensorless Fet Element DC Motor Driver," [online] [Retrieved on Oct. 9, 2006] Retrieved from the Internet<URL:http://robotx.sourceforge.net/bridge/bridge.shtml>.

Trost, F.J., "Energy-Storing Feet," JACPOC, 1989, vol. 24, No. 4, [online] [Retrieved on Oct. 9, 2006] Retrieved from the Internet<URL:http://jacpoc.oandp.com/library/1989_04_082.asp>.

* cited by examiner

SYSTEM AND METHOD OF PREDICTING NOVEL MOTION IN A SERIAL CHAIN SYSTEM

CROSS-REFERENCE TO RELATED APPLICATIONS

This application is a continuation-in-part of U.S. patent application Ser. No. 10/151,647 filed on May 16, 2002 now U.S. Pat. No. 7,135,003 which claims priority under 35 U.S.C §119(e) from U.S. provisional applications No. 60/301,891 filed on Jun. 29, 2001 and No. 60/353,378 filed on Jan. 31, 2002 which are all incorporated by reference herein in their entirety. This application is related to U.S. patent application Ser. No. 11/038,692, filed on Jan. 19, 2005, entitled "A System and Method of Estimating Joint Loads in a Three-Dimensional System" which is incorporated by reference herein in its entirety. This application is also related to U.S. patent application Ser. No. 11/038,978, filed on Jan. 19, 2005, entitled "A System and Method of Estimating Joint Loads Using an Approach of Closed Form Dynamics" which is incorporated by reference herein in its entirety.

FIELD OF THE INVENTION

The present invention relates to human motion analysis and synthesis. The present invention relates to inverse dynamics analysis, which uses knowledge of the motion of a dynamical system to determine applied forces and moments at joints. The present invention further relates to forward dynamics analysis, which provides the motion of a biomechanical system as a consequence of applied forces. The present invention further relates to a control theoretic framework for analysis and synthesis of human motion, whereby the estimation of internal forces and moments has been formulated as a trajectory tracking control problem.

BACKGROUND OF THE INVENTION

Studies of neuromuscular systems are typically concerned with either the synthesis or analysis of human motion (Delp and Loan, A Computational Framework for Simulating and Analyzing Human and Animal Movement, IEEE Computing in Science and Engineering, 2(5): 46-55, 2000; Thelen, Anderson and Delp, Generating Dynamic Simulations of Movement Using Computed Muscle Control, Journal of Biomechanics, 36:321-328, 2003, which are incorporated by reference herein in their entirety). The synthesis problem, referred to as forward dynamics analysis, attempts to provide the motion of a biomechanical system as a consequence of the applied forces and given initial conditions. The analysis, or inverse dynamics problem, can be viewed as the inverse of the synthesis problem and is conventionally used to estimate joint forces and joint moments. One or more forces or moments at a joint are referred to as joint loads.

In a conventional inverse dynamics analysis, joint forces and joint moments are calculated from the observation of segmental movement. Inverse dynamics analysis is conventionally applied to biomechanics problems because the internal forces of human joints cannot be readily measured. Segment movements, however, can be measured and joint angles can be inferred from the measured displacement to determine the corresponding joint forces and torques. Thus, inverse dynamics analysis is the conventional method used to gain insight into the net summation of all torques and all muscle activity at each joint.

A big challenge with using inverse dynamics in the study of human motion is the error caused by calculating higher-order derivatives to calculate joint forces and moments. Methods for using inverse dynamics concepts in biomechanics are well developed if the input signals are noise-free and the dynamic model is perfect. Experimental observations, however, are imperfect and contaminated by noise. Sources of noise include the measurement device and the joint itself. Inverse dynamics methods for calculating joint forces and moments require the calculation of higher order derivatives of experimental data contaminated by noise, which is a notoriously error prone operation (Cullum, Numerical Differentiation and Regularization, SIAM J. Numer. Anal., 8(2):254-265, 1971, which is incorporated by reference herein in its entirety). Specifically, the angular accelerations for a three-dimensional segment are the second derivatives of its joint angles and the linear accelerations of the segment are the second derivatives of its center of mass coordinates.

Numerical differentiation of the experimental observations amplifies the noise. The presence of high frequency noise is of considerable importance when considering the problem of calculating velocities and accelerations. When input signals with noise are differentiated, the amplitude of each of the harmonics increases with its harmonic number. When input signals are differentiated, the velocity signals increase linearly, while accelerations increase in proportion to the square of the harmonic number. For example, second order differentiation of a signal with high frequency noise $\omega$ can result in a signal with frequency components of $\omega^2$. The result of this parabolic noise amplification is erroneous joint force and joint moment calculations.

Although numerical schemes are available to provide estimates of higher order derivatives, the reliability of results is limited since there is no optimal solution or automatic method to filter biomechanical data (Giakas and Baltzopoulos, Optimal Digital Filtering Requires a Different Cut-Off Frequency Strategy for the Determination of the Higher Derivatives, Journal of Biomechanics, 30(8):851-855, 1997, which is incorporated by reference herein in its entirety). Although techniques exist for filtering the noise, filtering is difficult and time-consuming because much analysis is required to separate the true signal in the biomechanical data from the noise. For example, low-pass filtering is commonly used to reduce high frequency errors. A difficulty in low-pass filtering, however, is the selection of an optimal cutoff frequency $f_c$. Because there is no general solution for selecting optimal filter parameters, filtering techniques often produce unreliable results.

Optimization-based approaches have been proposed to estimate joint forces and joint moments without the errors associated with performing a conventional inverse dynamics analysis (Chao and Rim, Application of Optimization Principles in Determining the Applied Moments in Human Leg Joints during Gait, J. Biomechanics, 6:497-510, 1973, which is incorporated by reference herein in its entirety). Unlike inverse dynamics, optimization-based methods do not require numerical differentiation. However, the application of optimization-based solutions is limited because convergence and stability are not guaranteed, the methods are computationally expensive, and are generally too complex to implement.

Another problem with using inverse dynamics for analyzing human motion is that the inverse dynamics technique lacks the capability to predict the behavior of novel motions, a problem typically encountered in clinical applications. In inverse dynamics, forces and moments are calculated from observed responses. The prediction of novel motions involves calculating the response expected from the application of forces and moments. An inverse dynamics analysis lacks predictive capability because forces and moments are calculated rather than the expected response from the application of those forces and moments.

Another problem with certain inverse dynamics procedures that utilize only kinematic data is that they utilize whole-body solution. Parametric uncertainties in an upper body portion, including the physical parameters of the upper body portion or the effects of external loads, are significant sources of error in the estimation of joint forces and moments when using closed form, whole body dynamic procedures.

For a three-dimensional body, there is therefore a great need for a system and method for estimating joint loads without the errors caused by calculation of higher order derivatives of kinematic data with noise. What is further needed is a system and method for estimating joint forces and moments that does not necessarily require closed form, whole body analysis. Further, there is great need for a system and method for predicting human motions as a consequence of applied forces.

SUMMARY OF THE INVENTION

One embodiment of the present invention provides a method for estimating joint load at a joint of a segment. A joint load includes the forces and/or moments acting at a joint. The method comprises the steps of receiving kinematic data, determining a modified acceleration using at least the kinematic data, estimating a joint load using at least the modified acceleration; and determining simulated kinematic data for the segment using at least the joint load. The present invention thus addresses the problems with conventional inverse dynamics analysis by providing a forward dynamics solution for estimation of joint loads that is stable, guaranteed to converge, computationally efficient, and does not require acceleration computations.

Another embodiment of the present invention provides a method of predicting simulated kinematic data for a segment. The method comprises the steps of determining a modified acceleration using at least original kinematic data, estimating a joint load for a joint of the segment by using at least the modified acceleration, and predicting kinematic data for the segment based on one or more modified parameters. Therefore, one embodiment of the present invention advantageously allows for the prediction of novel motion.

According to one embodiment, modified acceleration may be computed by using one or more error values representing differences between measured kinematic data and previously simulated kinematic data. A feedback gain is applied to force the error values to zero. Therefore, an advantage of the present invention is that the modified acceleration is computed without the need for calculating higher order derivatives of noisy kinematic data, thereby for allowing for estimation or prediction of joint loads without the errors caused by calculation of higher order derivatives.

According to further embodiments, the step of estimating a joint load involves recursively estimating the joint loads at successive joints of a three-dimensional system. Recursive embodiments of the present invention are applicable to open chain systems as well as closed chain systems. Therefore, the present invention advantageously eliminates errors caused by parametric uncertainties during estimation of joint forces and moments using closed form, whole body dynamic procedures. According to other embodiments, the step of estimating a joint load involves estimating the joint load using closed form dynamics. Closed form embodiments of the present invention are applicable to open chain systems as well as closed chain systems.

DETAILED DESCRIPTION OF THE PREFERRED EMBODIMENTS

Various embodiments of the present invention provide for estimation of joint loads in multi-dimensional systems, for example estimation of joint loads in human beings. Various embodiments of the present invention also provide for prediction of motions such as prediction of human motion.

Various embodiments of the present invention include recursive dynamics, where joint loads are estimated iteratively from one segment to another, as well as closed form dynamics, where all joint loads are computed simultaneously. For example, the selection of a recursive embodiment versus a closed form embodiment may depend upon what sensors are available or on an application for which the invention is being used.

Embodiments of the present invention include open-chain systems and closed chain systems. In an open chain system, at most one end of the multi-body system is in contact with the environment. The other end or ends are free or unconstrained. In a closed chain system, more than one end is in contact with the environment.

Further, the present invention may be embodied variously using various sensing modalities. In an exemplary sensing modality, only kinematic measurements are available. In another exemplary sensing modality, both kinematic measurements and reaction force measurements are available.

I. Recursive Dynamics Embodiments

According to one embodiment, joint loads are estimated recursively for a three-dimensional serial chain. A serial chain system includes one or more segments that are connected together by joints, where reaction forces and moments at a joint are shared by the two segments connected at the joint. In recursive dynamics, one starts at a first end of a serial chain and calculates successive joint loads moving away from the first end. The joint load estimated for a first joint is used in estimating the joint load for the next joint until the joint or joints in interest are reached. That is, the output of a recursion is force and moment estimation for one or more joints of interest.

Figure 1:
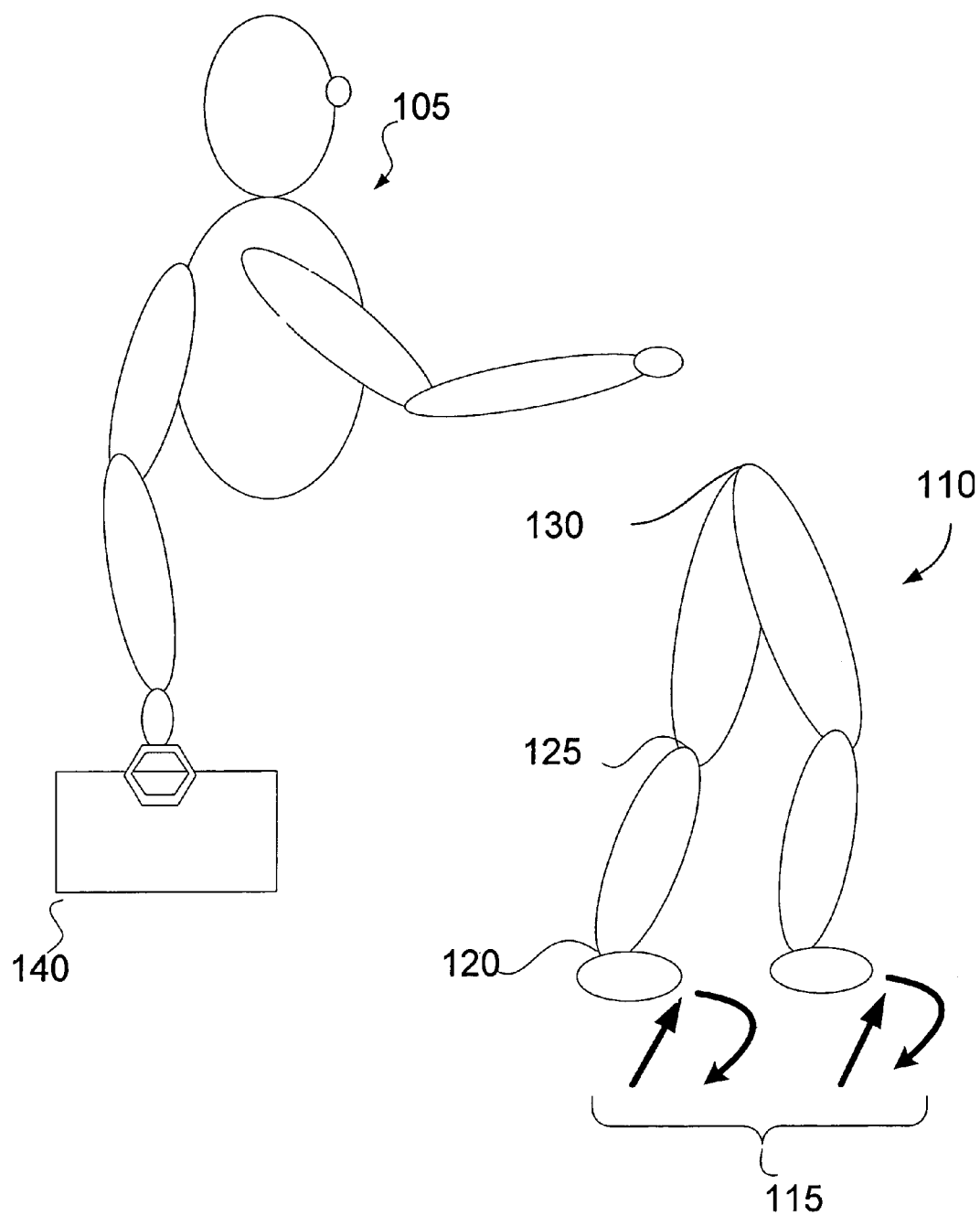
FIG. 1 shows how a recursive embodiment is used to separate lower body dynamics from upper body dynamics according to one embodiment of the present invention.

An advantage of using recursive dynamics is that it allows for estimation of joint loads at a particular joint of interest without the need to model the dynamics of the whole body. FIG. 1 is an illustration showing how a recursive embodiment is used to separate lower body dynamics from upper body dynamics. The illustration includes upper body portion 105 and lower body portion 110. A segment of upper body portion 105 is illustrated with load 140. Lower body portion 110 includes segments having ankle joint 120, knee joint 125, and hip joint 130. In a recursive embodiment for estimating joint forces and moments, the upper body portion 105 can be modeled separately from the lower body portion 110. Starting with measured reaction forces and moments 115, for example ground reaction forces and moments, the internal forces and moments acting on ankle joint 120, knee joint 125, and hip joint 130 can successively be estimated without considering the effects due to load 140 or the physical parameters of upper body portion 105, such as mass, center of mass, inertia, and segment dimensions. These parametric uncertainties in upper body portion 105 are significant sources of error in the estimation of the internal forces and moments in the human body when using closed form, whole body dynamic procedures. Although in a particular case it may be desirable to model whole body dynamics, the recursive embodiment provides the flexibility to focus on joints and segments of interest without introducing additional sources of error.

Further, measured reaction forces and moments 115 used in recursion provide an extra sensing modality. That is, measured reaction forces and moments 115 provide an additional cue that increases the reliability of the resulting internal force estimations. Human beings may be subjected to unpredictable loads or constrained dynamics resulting from interaction with other objects or other people in the environment. Such circumstances can alter the dynamic representation required to estimate the internal forces and moments at the joints. Some applications for using a recursive embodiment in these circumstances include performing biomechanical studies of lifting tasks and developing controls for assistive devices that aid the physically impaired in everyday tasks. One skilled in the art will appreciate that in-shoe force and pressure sensing devices are complementary technologies that can be used to provide extra sensing modalities for use in various force and moment estimations.

A. Recursive Dynamics Method for a Three-Dimensional Serial Chain System

Figure 2:
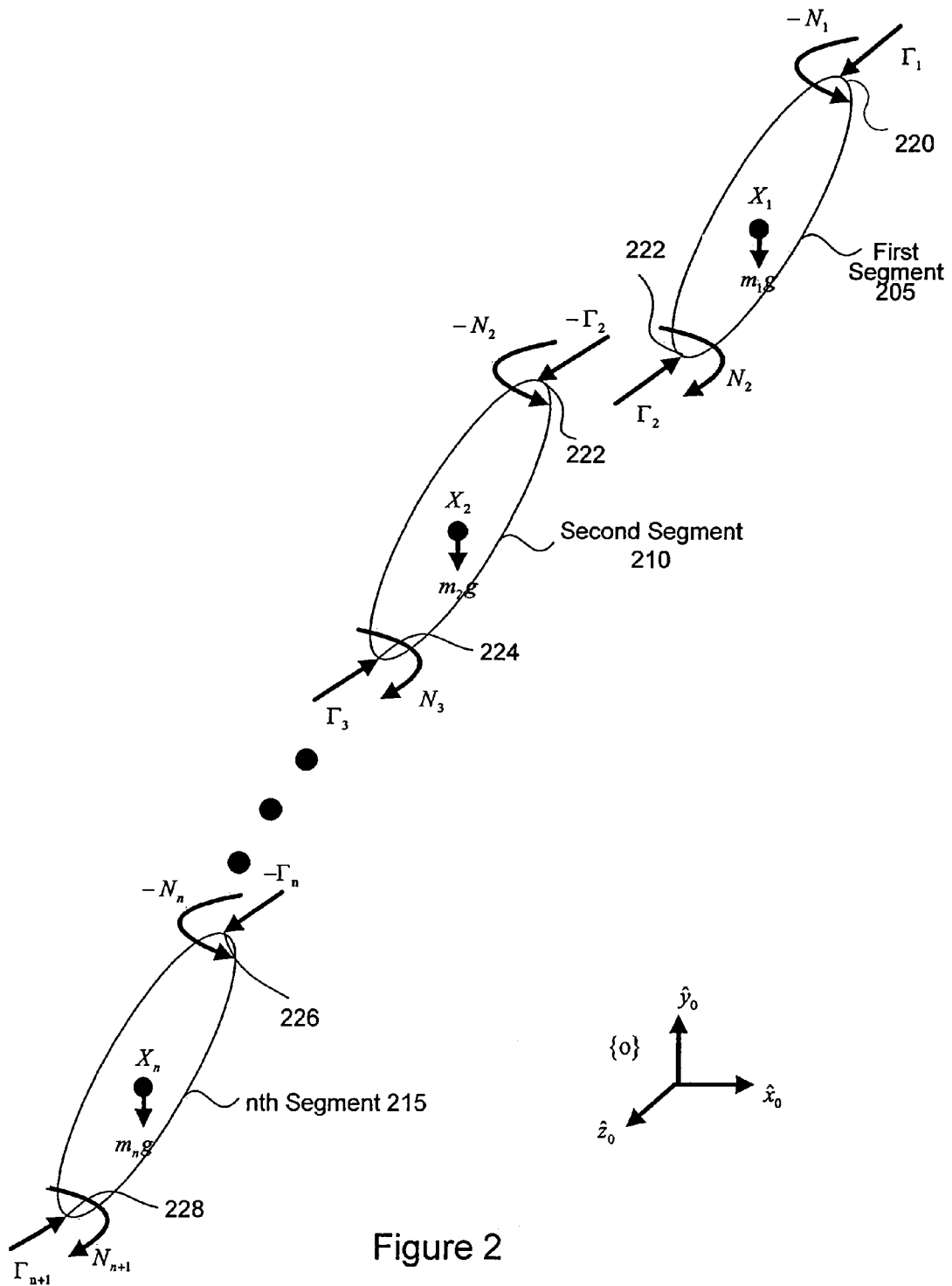
FIG. 2 is a free body diagram of forces acting on segments in an open chain, three-dimensional serial link system according to one embodiment of the present invention.

FIG. 2 is a free body diagram of forces acting on segments in an open chain, three-dimensional serial link system. The system includes first segment 205, second segment 210, and $n^{th}$ segment 215. The segments 205, 210 . . . 215 are linked by revolute joints. Each of segments 205, 210 and 215 is illustrated as a free body diagram in which first joint 220, second joint 222, third joint 224, $n^{th}$ joint 226 and $(n+1)^{th}$ joint 228 connect the segments. First segment 205 includes first joint 220 and second joint 222. Second segment 210 includes second joint 222 and third joint 224. $n^{th}$ segment 215 includes $n^{th}$ joint 226 and $(n+1)^{th}$ joint 228. In particular, segments 205 and 210 are connected as follows: second joint 222 links first segment 205 with second segment 210. Therefore, a serial chain of n segments is formed by connecting adjacent segments at their common or overlapping joint. The joint loads at a joint are shared by the segments connected at the joint.

The motion of the three-dimensional serial link system in FIG. 2 is described by two coordinate systems, a space-fixed or inertial coordinate system, and a moving body-fixed coordinate system that is rigidly fixed to each segment and participates in its motion. The frame descriptions for the inertial coordinate system and the body-fixed coordinate system are denoted by $\{O\}$ and $\{B_i\}$, respectively. Each segment's position relative to frame $\{O\}$ is described by the vector $X_i$. The notation of vectors written with a leading superscript indicates the coordinate system to which they are referenced. For example, $^iN_i$ represents a vector whose components have numerical values about the axis of frame $\{B_i\}$.

The force due to gravity acting at the $i^{th}$ segment's center of mass is denoted by $m_i g$, where $m_i$ is the mass of segment i and g is the 3×1 vector representing the acceleration due to gravity. The vectors $^OT_i$ and $^iN_i$ represent the force and moment couple exerted on segment i by segment i−1, with respect to frames $\{O\}$ and $\{B_i\}$ respectively. For example, with respect to second joint 222, the force $^OT_2$ and moment $^iN_2$ exerted by first segment 205 and second segment 210 on each other are illustrated. Similarly, the vector $^OT_{i+1}$ and $^iN_{i+1}$ represent the force and moment couple exerted on segment i by segment i+1.

With reference to FIG. 2, an instance of recursive calculation is now described. Recursive analysis begins at $n^{th}$ segment 215 by determining the forces and moments at $n^{th}$ joint 226. The estimated forces and moments at $n^{th}$ joint 226 are the output of the first step of the recursive analysis. This output is used as input for estimating the forces and moments at the next joint, i.e. the $(n-1)^{th}$ joint (not shown). In this manner, the recursive analysis of joint forces and moments at successive joints continues until the joint of interest is reached. According to one embodiment, measured ground reaction forces and moments are acting on $n^{th}$ segment 215, which is referred to as an end-effector segment, and the forces and moments acting on $n^{th}$ joint 226 are estimated in terms of the measured ground reaction forces and moments. Next, the forces and moments acting at the (n−1)h joint are estimated in terms of the previously estimated forces and moments acting at $n^{th}$ joint 226. This recursive procedure of using the output of the previous calculation as an input for the current calculation is repeated until forces and moments have been estimated for the joint or joints of interest. One skilled in the art will appreciate that first segment 205 is not necessarily an end segment in a multi-segment system. Rather, first segment 205 is the segment at which it is desired to stop the recursive computation if one is interested in obtaining estimates of the forces and moments at first joint 220. It should be further noted that measured reaction forces and moments 115 (FIG. 1) act at a point of contact with the environment, which is not necessarily a joint.

Figure 3:
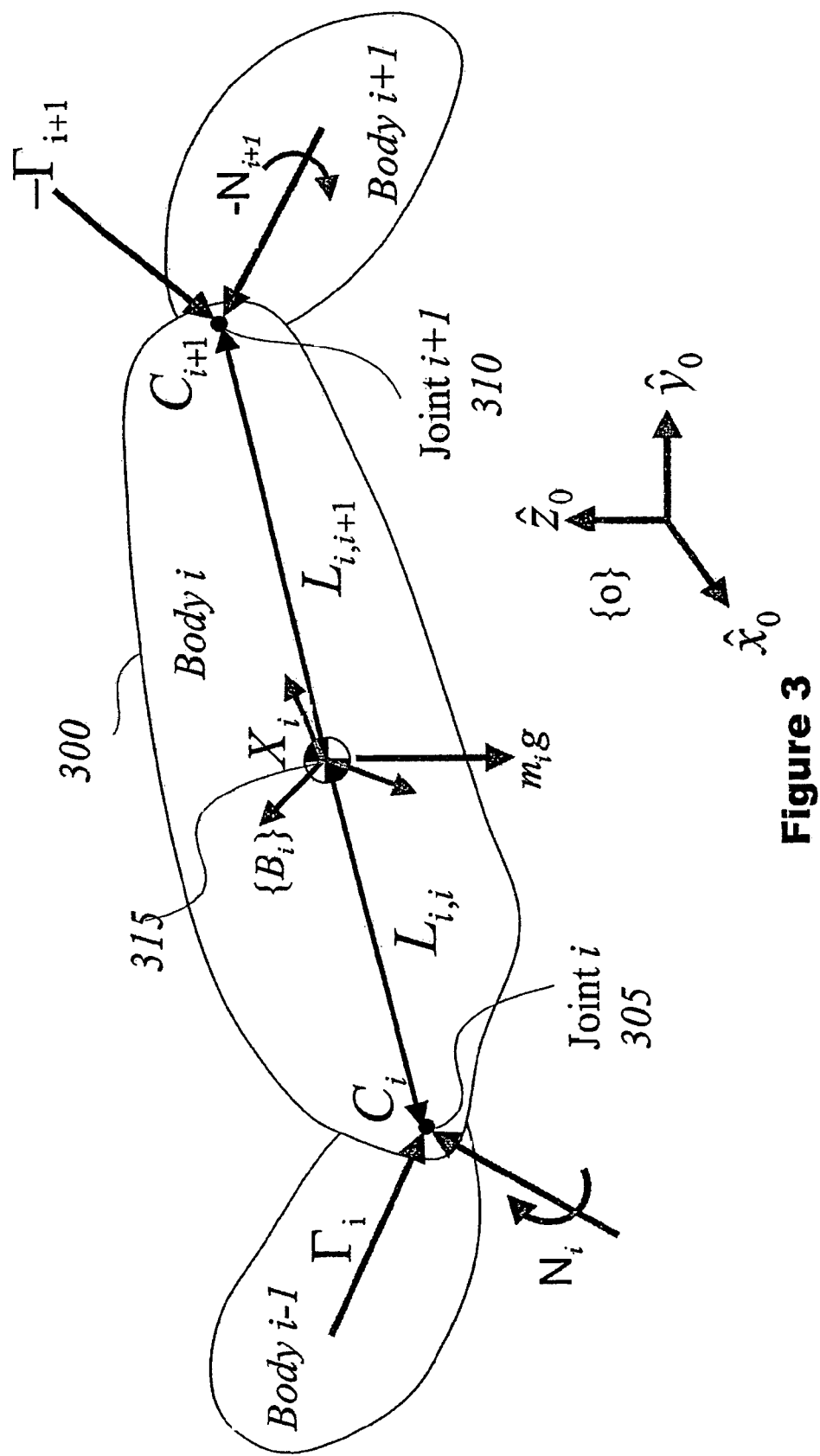
FIG. 3 is a free body diagram of one segment within a three-dimensional serial link system according to one embodiment of the present invention.

FIG. 3 is a free body diagram of one segment within a three-dimensional serial link system. $i^{th}$ segment 300 is one segment within a three-dimensional serial link system, such as the system illustrated in FIG. 2. As illustrated in FIG. 3, $i^{th}$ segment 300 includes joint i 305 and joint i+1 310. The origin of the frame $\{B_i\}$ represents the position of the $i^{th}$ segment's center of mass 315. The position of $i^{th}$ segment's center of mass 315 relative to frame $\{O\}$ is described by vector $X_i$. The joint centers at joint i 305 and joint i+1 310 are described by the vectors $C_i$ and $C_{i+1}$ respectively, with respect to frame $\{O\}$. The position vectors in frame $\{d\}$ from the $i^{th}$ segment's center of mass 315 to the connection points $C_i$ and $C_{i+1}$, are described by $L_{i,i}$ and $L_{i,i+1}$, respectively. The force due to gravity acting at the $i^{th}$ segment's center of mass 315 is denoted by $m_i g$, where $m_i$ is the mass of segment i and g is the 3×1 vector representing the acceleration of gravity. The vectors $^oT_i$ and $N_i$ represent the force and moment couple exerted on segment i by segment i−1, with respect to frames $\{O\}$ and $\{B_i\}$, respectively. Similarly, the vector $^oT_{i+1}$ and $^iN_{i+1}$ represent the force and moment couple exerted on segment i by segment i+1, with respect to frames $\{O\}$ and $\{B_i\}$, respectively.

B. Description of Rotation Transforms

The orientation of frame $\{B_i\}$ relative to frame $\{O\}$ is achieved through orthogonal matrix $^oR_i$, where the notation with the relative transformation is with respect to the frame with the leading superscript. The rotation matrix represents three consecutive rotations using Euler angles $\Theta=[\phi,\theta,\psi]^T$. Each rotation is performed about an axis of the moving reference frame. The explicit expression for the rotation matrix is given by equation 1 below, where the notations c and s represent sin and cos, respectively.

$$^oR_i = \begin{bmatrix} c\phi c\psi - s\phi c\theta s\psi & -c\phi s\psi - s\phi c\theta c\psi & s\phi s\theta \\ s\phi c\psi + c\phi c\theta s\psi & -s\phi c\psi + c\phi c\theta c\psi & -c\phi s\theta \\ s\theta s\psi & s\theta c\psi & c\theta \end{bmatrix} \quad (1)$$

The inverse transformation from frame $\{O\}$ to frame $\{B_i\}$ is give by equation 2 below.

$$^iR_o = {^oR_i}^{-1} = {^oR_i}^T \quad (2)$$

The Euler angles and their derivatives in terms of the angular velocity $W=[w_x, W_y, W_z]^T$ along the body fixed axes is given by equation 3 below.

$$\dot\Theta = H^{-1} W \quad (3)$$

$H^{-1}$ is defined in additional detail by equation 4 below.

$$H^{-1} = \begin{bmatrix} s\psi/s\theta & c\psi/s\theta & 0 \\ c\psi & -s\psi & 0 \\ -s\psi c\theta/s\theta & -c\psi c\theta/s\theta & 1 \end{bmatrix} \quad (4)$$

The inverse transformation is given by equation 5 below.

$$W = H\dot\Theta \quad (5)$$

H is defined in additional detail by equation 6 below:

$$H = \begin{bmatrix} s\theta s\psi & c\psi & 0 \\ s\theta c\psi & -s\psi & 0 \\ c\theta & 0 & 1 \end{bmatrix} \quad (6)$$

The angular acceleration $\dot W$ can be obtained by differentiating angular velocity W in equation 5 with respect to time. The angular acceleration $\dot W$ is given by equation 7 below.

$$\dot W = H\ddot\Theta + \dot H\dot\Theta \quad (7)$$

$\dot H$ is defined in additional detail by equation 8 below.

$$\dot H = \begin{bmatrix} \dot\psi s(\theta)c(\psi) + \dot\theta c(\theta)s(\psi) & -\dot\psi s(\psi) & 0 \\ -\dot\psi s(\theta)s(\psi) + \dot\theta c(\psi)c(\theta) & -\dot\psi c(\psi) & 0 \\ -\dot\theta s(\theta) & 0 & 0 \end{bmatrix}, \quad (8)$$

C. Derivation of Newton-Euler Equations

The Newton-Euler equations of motion are derived using special notation where the translational and rotational equations of motion are combined in vector and matrix form. Although, the equations are derived for isolated $i^{th}$ segment 300, which forms a serial chain with its two neighboring segments, those skilled in the art will recognize that the following derivation can be extended and recursively applied in any serial chain or branching chain mechanism with one or more segments. Further, consistent with most models of human anatomy, each joint is assumed to have three translational and three rotational degrees of freedom. Those skilled in the art will recognize that the following derivation is also applicable to other joint models.

For isolated $i^{th}$ segment 300, the Euler angles relative to frame $\{O\}$ are given by $\Theta_i = [\phi_i, \theta_i, \psi_i]^T$. The angular velocity for $i^{th}$ segment 300 is represented by $W_i = [w_{ix}, W_{iy}, w_{iz}]^T$, and the angular acceleration for $i^{th}$ segment 300 is represented by $\dot W_i$. The position of the center of mass 315 of the $i^{th}$ h segment 300 relative to frame $\{O\}$ is described by vector $X_i$, the linear acceleration of $i^{th}$ segment 300 is given by $\ddot X_i$, and the linear velocity of $i^{th}$ segment 300 is given by $\dot X_i$.

The Newton-Euler state space equations describing the motion of $i^{th}$ segment 300 about its center of mass 315 are set forth below in equation 9, equation 10 and equation 11. See Hemami, A State Space Model for Interconnected Rigid Bodies, IEEE Trans. on Automatic Control, 27(2): 376-382, 1982, which is incorporated by reference herein in its entirety. I is the inertia tensor of $i^{th}$ segment 300 in frame $\{B_i\}$, and $f(W) = W \times I\ W$ is the "gyroscopic torque".

$$m_i \ddot X_i = {^oT_i} - {^oT_{i+1}} - m_i g \quad (9)$$

$$\dot\Theta_i = H_i^{-1} W_i \quad (10)$$

$$I_i \dot{W}_i = -f(W_i) + {}^iN_i - {}^iN_{i+1} + {}^iR_o(L_{i,i} \times {}^o T_i) - {}^iR_o(L_{i,i+1} \times {}^o T_{i+1}) \quad (11)$$

One skilled in the art will appreciate that equation 9 represents an expression for summing the translational forces acting on segment 300, equation 10 represents the angular velocity of $i^{th}$ segment 300, and equation 11 represents an expression for summing the torques acting at joint i 305 and joint i+1 310.

To simplify notation and avoid using cross products, consider the following identity for cross product of arbitrary vectors a and b, where the tilde symbol () denotes the skew symmetric matrix representation of a vector.

$$a \times b = \tilde{a}b \quad (12)$$

For example, with the vector $L=[l_x, l_y, l_z]^T$ one can associate the 3×3 skew symmetric matrix $\tilde{L}$, defined by equation 13 below.

$$\tilde{L} = \begin{bmatrix} 0 & -l_z & l_y \\ l_z & 0 & -l_x \\ -l_y & l_x & 0 \end{bmatrix} \quad (13)$$

The representation of equation 11 with the new notation is expressed in equation 14 below.

$$I_i \dot{W}_i = -f(W_i) + {}^iN_i - {}^iN_{i+1} + {}^iR_o\tilde{L}_{i,i}{}^o T_i - {}^iR_o\tilde{L}_{i,i+1}{}^o T_{i+1} \quad (14)$$

Making use of equation 7 above and transforming ${}^iN_i$ and ${}^iN_{i+1}$ to frame {O}, equation 14 is expressed as equation 15 below.

$$I_i H_i \ddot{\Theta}_i = -f(W_i) - I_i \dot{H}_i \Theta_i + {}^iR_o{}^o N_i - {}^iR_o{}^o N_{i+1} + {}^iR_o\tilde{L}_{i,i}{}^o T_i - {}^iR_o \tilde{L}_{i,i+1}{}^o T_{i+1} \quad (15)$$

Combing the translational equations of motion, equation 9, and the rotational equations of motion, equation 15, we obtain a compact representation in matrix form of the Newton-Euler equation for an isolated body segment, which is set forth in equation 16 below. Vector $q_i=[X_i\Theta_i]^T$ represents the coordinates of the center of mass 315 of $i^{th}$ segment 300 and the Euler angles of the $i^{th}$ segment 300. One skilled in the art will appreciate that the term $\ddot{q}_i$ in equation 16 represents the second derivative of vector $q_i$, and $\dot{q}_i$ in equation 16 represents the first derivative of vector $q_i$.

$$M_i(q_i)\ddot{q}_i = P_i(q_i, \dot{q}_i) + A_{p_i}(q_i)U_i + A_{d_i}(q_i)U_{i+1} \quad (16)$$

The individual elements of equation 16 are defined in additional detail in equations 17 through 22. In equation 16, the notation $\bar{I}$ represents the 3×3 identity matrix, and $\emptyset$ represents the 3×3 matrix with all zero elements. $U_i$ is a vector whose elements represent the forces and moments acting at joint i 305 of $i^{th}$ segment 300, and $U_{i+1}$ is a vector whose elements represent the forces and moments acting at joint i+1 310 of $i^{th}$ segment 300.

$$M_i(q_i) = \begin{bmatrix} m_i \bar{I} & \emptyset \\ \emptyset & I_i H_i \end{bmatrix} \quad (17)$$

$$A_{d_i}(q_i) = \begin{bmatrix} -\bar{I} & \emptyset \\ -{}^iR_o\tilde{L}_{i,i+1} & -{}^iR_o \end{bmatrix} \quad (18)$$

$$A_{p_i}(q_i) = \begin{bmatrix} \bar{I} & \emptyset \\ {}^iR_o\tilde{L}_{i,i} & {}^iR_o \end{bmatrix} \quad (19)$$

$$P_i(q_i, \dot{q}_i) = \begin{bmatrix} -m_i g \\ -I_i \dot{H}_i \dot{q}_i - f(W_i) \end{bmatrix} \quad (20)$$

-continued $$U_i = \begin{bmatrix} {}^o T_i \\ {}^o N_i \end{bmatrix} \quad (21)$$

$$U_{i+1} = \begin{bmatrix} {}^o T_i \\ {}^o N_{i+1} \end{bmatrix} \quad (22)$$

D. Inverse Dynamics Problem

In inverse dynamics analysis, forces and moments acting at joints are computed from measured or desired kinematic data. One skilled in the art will recognize that statistical or geometric approaches operating on measured marker positions may be used to obtain the measured generalized coordinates for each segment, which are represented as $q_{m_i}$, where i is the segment number. As explained above, $q_{m_i}$ represents the three coordinates and the three Euler angles for $i^{th}$ segment 300. The vector of all generalized coordinates from segment i to segment n is expressed as $q_m$ in equation 23 below.

$$q_m = [q_{m_i}^T q_{m_{i+1}}^T \ldots q_{m_n}^T]^T \quad (23)$$

Referring to FIG. 2, an inverse dynamics analysis may be performed based on inward recursions starting from $n^{th}$ segment 215 and working inward toward the joint of interest, for example $i^{th}$ joint 305. Pursuant to an inverse dynamics analysis, the forces and moments at joints n through i can be computed using recursion equation 24 below, which has been derived from equation 16 above. According to one embodiment, the measured generalized coordinates for each segment, $q_m$, as well as their derivatives are known, as are the measured reaction forces and moments acting on $n^{th}$ segment 215, which are represented as $U_{n+1}$. These known parameters are used as inputs in recursion equation 24.

$$U_i = A_p^{-1}(q_{m_i})\{M_i(q_{m_i})\ddot{q}_i - P_i(q_{m_i}, \dot{q}_{m_i}) - A_{d_i}(q_{m_i})U_{i+1}\} \quad (24)$$

The inverse dynamics analysis allows us to calculate the vector U, shown in equation 25 below, of forces and moments at joints n through i.

$$U = [U_i^T U_{i+1}^T \ldots U_n^T]^T \quad (25)$$

E. Forward Dynamics Solution

Various embodiments of the present invention provide a control theoretic framework for analysis and synthesis of human motion, whereby estimation and synthesis of human motion has been formulated as a trajectory tracking control problem. Various embodiments of the present invention provide a tracking controller whose output represents the forces and moments that when applied to a forward dynamics module will reproduce or "track" the measured kinematic data. The tracking controller estimates the joint loads necessary to force a biomechanical system to track measured kinematics. The desired tracking is achieved by employing a nonlinear control law that linearizes and decouples every state such that the tracking error can be forced to zero. Tracking methods have been previously used in the robotics community for the purpose of manipulator control, as explained in Craig, Introduction to Robotics, Mechanics and Control, Addison-Wesley, $2^{nd}$ ed., 1989, which is hereby incorporated by reference in its entirety. Various embodiments of the present invention apply the concept of feedback linearization to estimate joint torques for human motion analysis and synthesis. Various embodiments of the present invention apply the concept of feedback linearization to predict human motions. Embodiments of the tracking controller for closed form computations are presented below. Embodiments of the tracking controller for recursive estimation are now explained with reference to FIG. 4.

Figure 4:
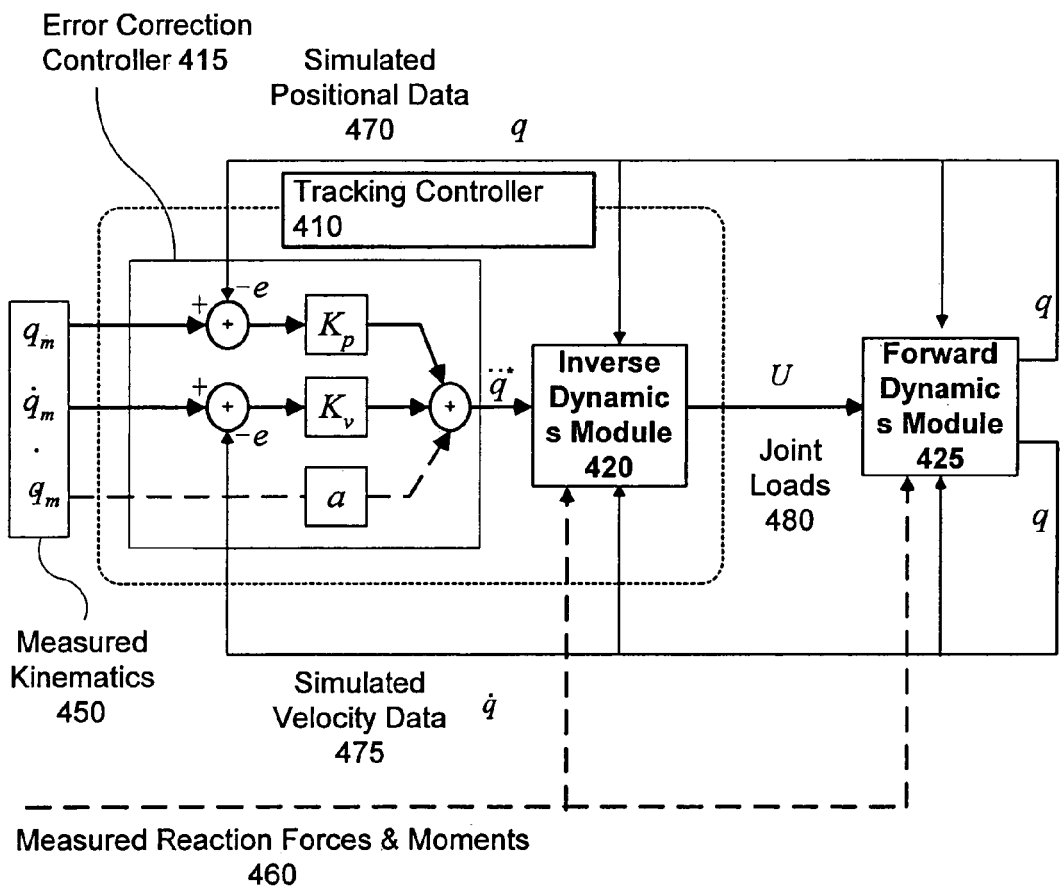
FIG. 4 is a block diagram of a tracking system for analysis and synthesis of human motion according to one embodiment of the present invention.

FIG. 4 is a block diagram of one embodiment of a tracking system for analysis and synthesis of human motion. With reference to an exemplary three-dimensional serial chain system in FIG. 2, the tracking system of FIG. 4 provides for estimation of joint loads at a particular time by using the following information: simulated kinematic data in the form of simulated state variables that were calculated using joint loads estimated for some previous instant in time; and measured kinematic data as well as their derivatives at the particular time. The tracking system in FIG. 4 comprises tracking controller 410 and forward dynamics module 425. Tracking controller 410 comprises error correction controller 415 and inverse dynamics module 420.

Error Correction Controller 415

Inputs to error correction controller 415 include measured kinematics 450, including measured positional data $q_m$, and measured velocity data $\dot{q}_m$ that are estimated by numerical differentiation of the kinematic data. Acceleration kinematic data $\ddot{q}_m$, which are estimated by numerical differentiation of measured velocity data, can be used in noise free applications, but are not required. For an exemplary three-dimensional serial chain system having n segments, measured kinematic data $q_m$ represents an n*6 matrix that provides the three measured Euler angles and three measured center of mass coordinates for each segment. Velocity kinematic data $\dot{q}_m$ represents an n*6 matrix that provides measured velocities of the three Euler angles and three center of mass coordinates for each segment. Similarly, acceleration kinematic data $\ddot{q}_m$ represents an n*6 matrix that provides accelerations of the three Euler angles and three center of mass coordinates for each segment. In FIG. 4, measured kinematics 450 represent the kinematics for each segment at a present instant in time for which tracking is being performed.

According to one embodiment, simulated kinematic data comprises simulated state variables q and $\dot{q}$, and inputs to error correction controller 415 also include simulated state variables q and $\dot{q}$ that are obtained as a result of forward dynamics simulations. For an exemplary three-dimensional serial chain system having n segments, simulated positional data q 470 represents an n*6 matrix that provides the three simulated Euler angles and three simulated center of mass coordinates for each segment. Similarly, simulated velocity data $\dot{q}$ 475 represents an n*6 matrix that provides simulated velocities of the three Euler angles and three center of mass coordinates for each segment.

Simulated positional data q 470 represents simulated positional data for the present instant in time for which tracking is being performed, and is calculated using joint loads 480, simulated state variables and (optionally) measured reaction forces and moments 460 at a previous instant in time, as explained below. Simulated velocity data $\dot{q}$ 475 represents simulated velocity data for the present instant in time for which tracking is being performed, and is calculated using joint loads 480, simulated state variables and (optionally) measured reaction forces and moments 460 at a previous instant in time, as explained below.

In the illustrated embodiment, error correction controller 415 comprises modules that implement equation 26 below. For each segment, error correction controller 415 compares measured positional data at the present time instant to simulated positional data 470 for the present time instant to obtain a positional error signal e. For each segment, positional error signal e represents positional errors for the three Euler angles and the three coordinates of the center of mass. Similarly, error correction controller 415 compares measured velocity data at the present time to simulated positional data 470 for the present time to obtain a velocity error signal $\dot{e}$. For each segment, velocity error signal $\dot{e}$ represents velocity errors for the three Euler angles and the three coordinates of the segment's center of mass.

The error signals are modulated by position and velocity feedback gain matrices $K_{pi}$ and $K_{v_i}$ and summed to arrive at an acceleration term $\ddot{q}^*_i$ that is an estimate (or modification) of the accelerations of the generalized coordinates. The modified acceleration term for each segment at the present instant in time is given by equation 26 below.

$$\ddot{q}^*_i = a\ddot{q}_{m_i} + K_{pi}(q_{m_i} - q_i) + K_{v_i}(\dot{q}_{m_i} - \dot{q}_i) \quad (26)$$

The feedback matrices $K_{v_i}$ and $K_{pi}$ are diagonal matrices, the details of which are chosen based on experimental observation to achieve a critically damped response. The relation between $K_v$ and $K_p$ to achieve a critically damped response is given by equation 27 below.

$$K_v = 2\sqrt{K_p} \quad (27)$$

The parameter a is a scalar parameter that may be set to zero or one. According to one embodiment, a=1 and measured accelerations are used to compute the modified acceleration term. According to another embodiment, a=0 and measured accelerations are ignored. One skilled in the art will appreciate that when parameter a is set equal to zero the second derivative of the kinematic data, the estimated accelerations term $\ddot{q}_{m_i}$ is ignored in equation 26. Therefore, in such a case, only modified acceleration $\ddot{q}^*_i$ is used in the tracking system. An advantage of not using the second derivative of noisy kinematic data is improved accuracy of force and moment estimation.

The modified acceleration for each segment in a three-dimensional system is concisely represented by vector array $\ddot{q}^*$, as shown in equation 28 below. Error correction controller 415 outputs modified acceleration $\ddot{q}^*$ as an input to inverse dynamics module 420.

$$\ddot{q}^* = [\ddot{q}^{*T}_i \ddot{q}^{*T}_{i+1} \ldots \ddot{p}^{*T}_n]^T \quad (28)$$

Inverse Dynamics Module 420

In addition to modified acceleration $\ddot{q}^*$, inputs to inverse dynamics module 420 include simulated state variables q and $\dot{q}$. Measured reaction forces and moments 460 may optionally be included as additional inputs to inverse dynamics module 420. According to one embodiment, measured reaction forces and moments comprise ground reaction forces and moments at the constrained end of a three-dimensional serial chain system. According to an exemplary embodiment, joint loads (U 480 at the present instant in time are estimated using inverse dynamics module 420. The vector U represents a matrix of joint forces and moments at one or more joints of an exemplary serial chain system. The joint loads at an exemplary $i^{th}$ joint may be represented as $U_i$. According to one embodiment, the joint loads $U_i$ that will drive body segment i to follow the desired trajectory $q_{m_i}$ (obtained from measurements) is obtained by the control law in equation 29 below. The structure of equation 29 differs from the inverse dynamics solution in equation 24 in that the input parameters are functions of measured feedback rather than measured kinematics data.

$$U_i = A_p^{-1}(q_i)\{M_i(q_i)\ddot{q}^*_i - P_i(q_i, \dot{q}_i) - A_{d_i}(q_i)U_{i+1}\} \quad (29)$$

According to one embodiment, for each time instant for which inverse dynamics analysis is being performed, inverse dynamics module 420 recursively applies the control law in equation 29 to estimate the joint loads at successive joints of a serial chain system. As seen in equation 29, inverse dynamics module 420 uses the joint loads $U_{i+1}$ at an $(i+1)^{th}$ joint to estimate the joint loads $U_i$ at a neighboring $i^{th}$ joint. In this manner, inverse dynamics module 420 recursively estimates the joint loads from an $n^{th}$ joint of an end effector segment until the joint loads at an $i^{th}$ joint of interest have been determined. According to another embodiment, joint loads (U) 480 at one or more joints are estimated using closed form dynamics, as explained in more detail below. The output of inverse dynamics module 420, representing the estimated joint loads at joints i . . . n is given by equation 30 below.

$$U = [U_i^T U_{i+1}^T \ldots U_n^T]^T \quad (30)$$

Forward Dynamics Module 425

Inputs to forward dynamics module 425 include joint loads U for the present instant in time for which analysis is being performed. Additionally, the simulated state variables q and $\dot{q}$ for the present instant in time are also used as input by forward dynamics module 425. According to one embodiment, when the tracking system in FIG. 4 is applied to obtain estimated joint loads (U) 480, the parameters for the forward dynamics module 425 (such as $P_i$, $M_i$, $A_{pi}$ and $A_{d_i}$) are identical to the parameters used by inverse dynamics module 420.

Forward dynamics module 425 computes induced accelerations $\ddot{q}_i$ at an exemplary $i^{th}$ joint of interest, for the present time instant for which analysis is being performed, according to equation 31 below. The vector containing the induced accelerations at joints i . . . n is given by equation 32 below.

$$\ddot{q}_i = M_i^{-1}(q_i)[P_i(q_i, \dot{q}_i) + A_{pi}(q_i) + A_{d_i}(q_i)U_{i+1}] \quad (31)$$

$$\ddot{q} = [\ddot{q}_i^T \ddot{q}_{i+1}^T \ldots \ddot{q}_n^T]^T \quad (32)$$

Matrices $M_i$, $P_i$, $A_{pi}$ and $A_{d_i}$ have been defined above in equations 17 through 20. Vectors $L_{i,i}$ and $L_{i,i+1}$ in these matrices are computed according to equations 33 and 34 below, where the measured joint centers, $C_{m_i}$ and $C_{m_{i+1}}$, are used as constraints to avoid numerical drift. One skilled in the art will recognize that the measured joint centers are derived from measured kinematics and anthropometric measurements. According to one embodiment, the measured joint centers may be obtained statistically based on regression equations. According to another embodiment, the measured joint centers may be obtained geometrically based on functional methods.

$$L_{i,i} = C_{m_i} - X_i \quad (33)$$

$$L_{i,i+1} = C_{m_{i+1}} - X_i \quad (34)$$

Having obtained the induced acceleration for the present time instant, t, for which analysis is being performed, forward dynamics module 425 performs a simulation to determine state variables $q_i$ and $\dot{q}_i$ for a next instant in time, t+Δt, based on available estimated joint loads U 480 and available simulated state variables for the present instant in time. According to one embodiment, forward dynamics module 425 performs numerical integration of the induced accelerations for each segment to obtain the simulated state variables (simulated positional and velocity data) for each segment at the next instant in time for which analysis is being performed, i.e. at t+Δt. In one embodiment, numerical integration is performed by an integration function in MATLAB software that is commercially available from The MathWorks, Inc., Natick, Mass. One skilled in the art will appreciate that integration can be performed by many methods, such as the Runge Kutta method.

As described above, forward dynamics module 425 obtains simulated state variables q and $\dot{q}$ for the next instant in time by numerical integration of the induced accelerations for the present instant in time. The state variables q and $\dot{q}$ are input to error correction controller 415, to be used in determining modified acceleration $\ddot{q}^*$ for the next time step. Error correction controller 415 generates modified accelerations $\ddot{q}^*$ such that the inverse dynamics module 420 computes a set of inputs or controls denoted by U that when applied to forward dynamics module 425 substantially reproduces or tracks the measured kinematics 450.

For a desired time period of human motion analysis, the tracking system in FIG. 4 forces the tracking error between simulated and measured kinematics to approach zero as time progresses, thereby ensuring the accuracy of estimated joint loads. According to one embodiment, the system is initialized by setting the simulated state variables at time t=0 equal to the measured kinematics 450 at t=0.

One skilled in the art will appreciate that the described equations, expressions, modules, or functions can be implemented in a general-purpose computer, special purpose computer, or hardware. In an embodiment, a software programmable general-purpose computer implements features of the invention. The software is preferably distributed on a computer readable medium, which includes program instructions. A computer readable medium includes, for example, a computer readable storage volume. The computer readable storage volume can be available via a public computer network, a private computer network, or the Internet. One skilled in the art will appreciate that the program instructions can be in any appropriate form, such as source code, object code, or scripting code.

Figure 5:
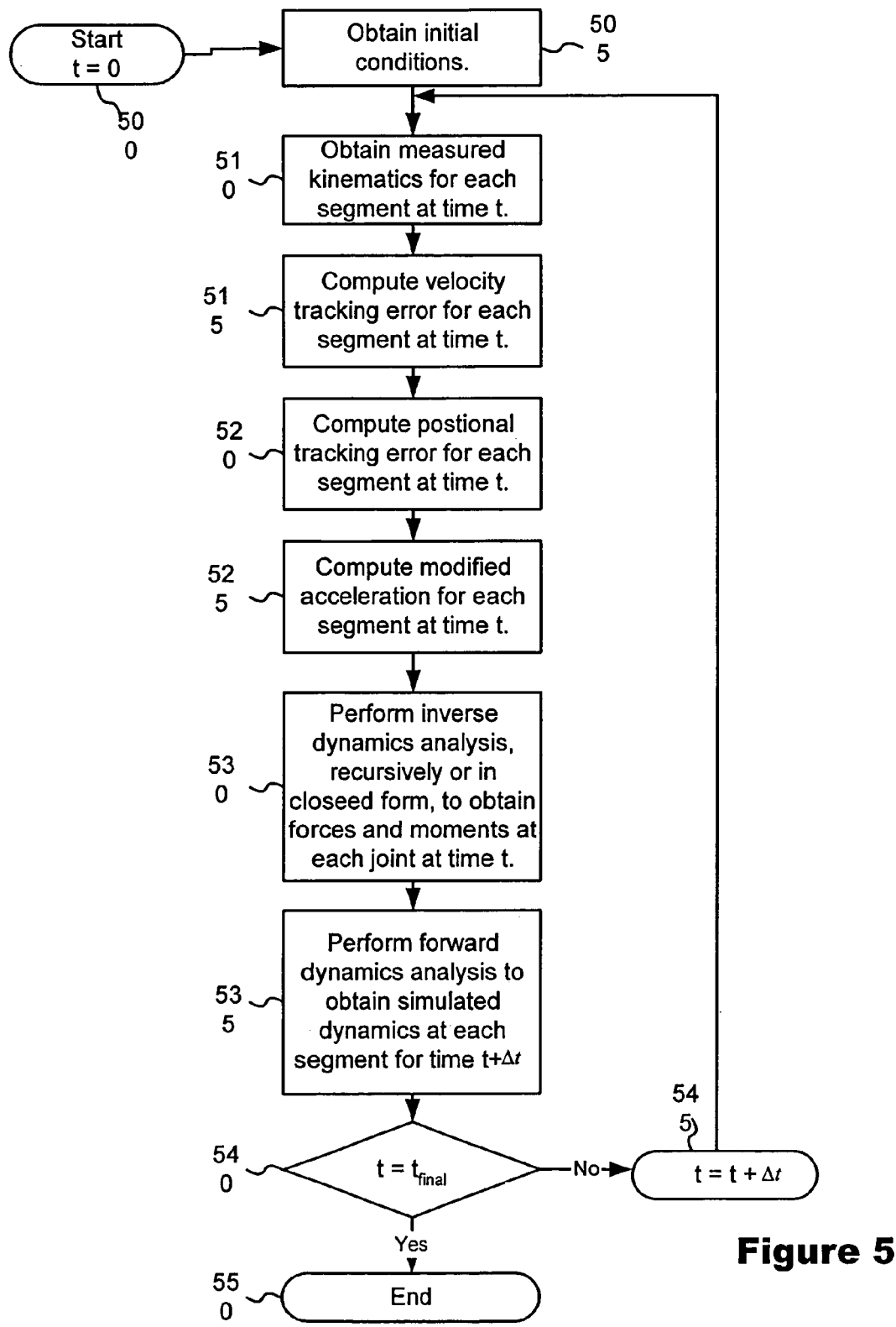
FIG. 5 is a flowchart illustrating a tracking process used for a desired time period of human motion analysis according to one embodiment of the present invention.

FIG. 5 is a flowchart illustrating a tracking process used for a desired time period of human motion analysis according to one embodiment of the present invention. The flowchart in FIG. 5 is explained with reference to an exemplary three-dimensional serial chain system described in FIG. 2 and with reference to an exemplary $i^{th}$ segment 300 described in FIG. 3. The start 500 of the tracking process occurs at an initial time, t=0, chosen as the time to start estimating joint loads at joints of one or more segments. The process starts by obtaining initial conditions 505 that represent initial values of simulated state variables q and $\dot{q}$. According to an exemplary embodiment, the initial conditions are obtained from measured kinematic data by setting the initial values of simulated kinematics to be equal to the initial values of measured kinematics, as shown in equations 35 and 36 below.

$$q(t=0) = q_m(t=0) \quad (35)$$

$$\dot{q}(t=0) = \dot{q}_m(t=0) \quad (36)$$

For a present instant in time at which a serial chain system's motion is being analyzed, the process obtains measured kinematics 510 for each segment in the chain. One skilled in the art will recognize that statistical or geometric approaches operating on measured marker positions may be used to obtain the measured generalized coordinates for each segment, which are represented as $q_m$. Velocity kinematic data $\dot{q}_m$, and acceleration kinematic data, $\ddot{q}_m$, are estimated by numerical differentiation of the kinematic data. Next, the process computes velocity tracking error, $\dot{e}$, 515 for each segment at the present instant in time. For each segment, velocity tracking error $\dot{e}$ is computed by comparing velocity kinematic data at the present time instant to simulated velocity data 475 for the present time instant. As described above, velocity error signal $\dot{e}$ represents velocity errors for the three Euler angles and the three coordinates of the center of mass. Similarly, the process computes positional tracking error, e, 520 for each segment at the present instant in time. For each segment, positional tracking error e is computed by comparing measured positional kinematic data at the present time instant to simulated positional data 470 for the present time instant. As described above, positional error signal e represents positional errors for the three Euler angles and the three coordinates of the center of mass.

The process computes modified acceleration 525 for each segment at the present time instant using equation 26 above. According to one embodiment, the scalar a is set to zero in equation 26, thereby ignoring acceleration kinematic data during the tracking process and improving the accuracy of force and moment estimations. Modified accelerations computed at step 525 are used to perform inverse dynamics analysis 530, thereby obtaining estimated forces and moments at each joint for the present instant in time. According to one embodiment, the step of performing inverse dynamics analysis 530 recursively estimates the forces and moments at each joint of a serial chain system according to equation 29. According to another embodiment, the step of performing inverse dynamics analysis uses closed form analysis to estimate the forces and moments at each joint of a serial chain system. Further details of a closed form embodiment are explained below.

At step 535, the process performs forward dynamics analysis to obtain the simulated state variables (simulated kinematic data) for each segment at the next instant in time for which human motion analysis is desired. Forward dynamics analysis 535 has been explained in further detail above with reference to forward dynamics module 425.

Once simulated kinematics have been obtained, at step 540 the process determines whether the desired time period for human motion analysis has ended, i.e. whether $t=t_{final}$? If not, then the process selects the next instant in time for which joint loads are to be estimated by incrementing the present time instant, t, by $\Delta t$ at step 545, followed by repeating steps 510 through 540 of the tracking process described above to estimate the forces and moments at the joints of the serial chain system at the newly selected instant in time. If the desired time period for human motion analysis has ended, then the process ends at step 550.

F. Closed Loop Error Dynamics

Various embodiments of the present invention provide a tracking system for analysis and synthesis of human motion that employs a feedback control law described by equation 29 above. To demonstrate the tracking performance of this system, it is instructive to consider the closed loop error dynamics. The closed loop response and the associated error dynamics of tracking controller 410 may be described by a linear system. As shown in equation 37 below, positional error signal $e_i$ denotes the error between the measured kinematics $q_{m_i}$ and the simulated state variable $q_i$, which is obtained by integration in forward dynamics module 425. The error dynamics for several scenarios are described below.

$$e_i = q_{m_i} - q_i \qquad (37)$$

Accelerations are included: a=1

In the ideal situation of perfect measurements and zero error in numerical differentiation, the closed loop error dynamics is given by differential equation 38 below.

$$\ddot{e}_i + K_{v_i}\dot{e}_i + K_{pi}e_i = 0 \qquad (38)$$

The error dynamics of state variable $q_i$ can be independently controlled by eigenvalue assignment. Let $\lambda_1$ and $\lambda_2$ denote the eigenvalues of the above differential equation 38. Equation 39 provides a critically damped solution, i.e. no sinusoidal oscillations, with real and equal eigenvalues. This solution yields the fastest non-oscillatory response. As described above, the relationship between $K_p$ and $K_v$ to achieve a critically damped response is set forth in equation 27 above.

$$e(t) = c_1 e^{\lambda_1 t} + c_2 t e^{\lambda_2 t} \qquad (39)$$

Accelerations Ignored: a=0

Suppose the measured accelerations that are estimated from the measured kinematics are ignored by setting a=0. The closed loop error dynamics is expressed by non-homogeneous differential equation 40 below.

$$\ddot{e}_i + K_{v_i}\dot{e}_i + K_{pi}e_i = \ddot{q}_{m_i} \qquad (40)$$

Although the solution to the above differential equation 40 contains a forcing term, assuming the acceleration term $\ddot{q}_{m_i}$ is bounded, the error will converge to zero by assigning the eigenvalues of equation 40 to have negative and real parts. As before, the gains $K_{pi}$ and $K_{v_i}$ may be appropriately designed for a critically damped response using the relation given in equation 27 above.

Incorporating Derivative Estimation Error

In the above formulation of the error equations, it was assumed that the velocity kinematic data $\dot{q}_{m_i}$ and accelerations kinematic data $\ddot{q}_{m_i}$ can be precisely calculated by differentiating the measured positional data $q_m$. Indeed, errors in numerical differentiation of noisy kinematic measurements cannot be ignored and are considered in the following formulation.

Let $\epsilon_v$ and $\epsilon_a$ represent the bounded error in the velocity and acceleration calculations. The estimates $$\hat{\dot{q}}_{m_i}$$

and $$\hat{\ddot{q}}_{m_i}$$

may be expressed by equations 41 below.

$$\hat{\dot{q}}_{m_i} = \dot{q}_{m_i} + \epsilon_v \qquad (41)$$
$$\hat{\ddot{q}}_{m_i} = \ddot{q}_{m_i} + \epsilon_a$$

The closed loop dynamics incorporating the derivative estimation error is given by equation 42 below.

$$a\hat{\ddot{q}}_{m_i} - \ddot{q}_i + K_{v_i}(\hat{\dot{q}}_{m_i} - \dot{q}_i) + K_{p_i}(q_{m_i} - q_i) = 0 \quad (42)$$

Substituting equations 41 into equation 42, equation 43 below is derived.

$$a\hat{\ddot{q}}_{m_i} - \ddot{q}_i + K_{v_i}(\hat{\dot{q}}_{m_i} - \dot{q}_i) + K_{p_i}(q_{m_i} - q_i) = -(a\varepsilon_a + K_{v_i}\varepsilon_v) \quad (43)$$

The error dynamics for a=0 and a=1 are given by equations 44 and 45 below, respectively.

$$\ddot{e}_i + K_{v_i}\dot{e}_i + K_{p_i}e = -K_{v_i}\epsilon_v + \ddot{q}_{m_i}a = 0 \quad (44)$$

$$\ddot{e}_i + K_{v_i}\dot{e}_i + K_{p_i}e = -(\epsilon_a + K_{v_i}\epsilon_v)a = 1 \quad (45)$$

G. Open Chain and Closed Chain Embodiments

Recursive embodiments of the present invention include both open chain and closed chain estimations. An open chain system is constrained with the environment at one end, while the remaining terminal segments are free. A closed chain system has more than one end in contact with the environment. A recursive embodiment has been described with reference to FIG. 2 above, wherein the joint loads at successive joints are computed recursively starting with an $n^{th}$ joint 226 and ending with a joint of interest, such as the first joint 220. An advantage of a recursive formulation is that the entire body need not be modeled. The force and moment estimation is complete at the segment of interest regardless of whether the segment of interest is the last segment of the serial system. As described above with reference to FIG. 1, the parametric uncertainties in upper body portion 105 are significant sources of error in the estimation of internal forces and moments. The uncertainties can be avoided, however, when only joint moments proximal to the force plate are desired.

In one recursive embodiment of the present invention, open chain estimation is performed. In an open chain system, the one end in contact with the environment is termed a constrained end. In an embodiment of the present invention, the constrained end is a human being's foot that is in contact with the ground or other supporting surface.

In another recursive embodiment of the present invention, closed chain estimation is performed. A closed chain system has more than one end in contact with with the environment. Referring to FIG. 2, with force plate measurements for $n^{th}$ segment 215 available, the joint loads at the joint of interest are computed recursively with equation 29 above, starting with $n^{th}$ joint 226 and working towards the joint of interest.

II. Multi-Modal Embodiments

Since the optimal representation of the dynamic equations of motion will differ depending on the available sensors, inverse dynamics is in general considered a multi-modal sensing problem. See Dariush, Hemami and Parnianpour, Multi-modal Analysis of Human Movement from External Measurements, Journal of Dynamic Systems, Measurement and Control, 123(2): 272-278, 2002, which is incorporated by reference herein in its entirety. The tracking system of the present invention may be embodied using various modes of sensing. FIG. 6 depicts two exemplary modes of sensing having three different system level structures. Tracking error 605 in FIG. 6 represents positional tracking error e and velocity tracking error ė.

Figure 6A:
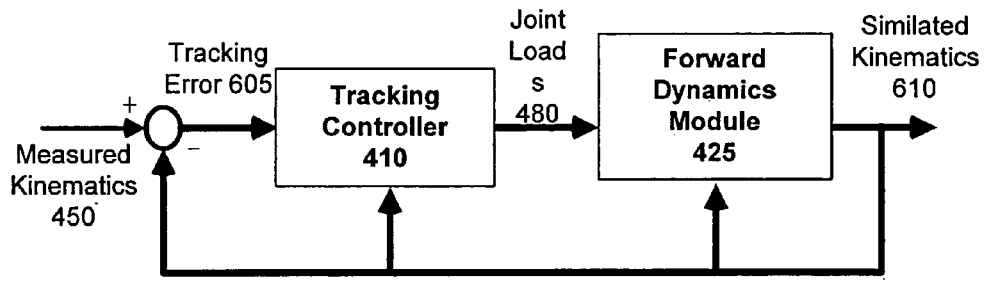
FIG. 6A is a block diagram of a tracking system where a serial chain system is modeled as an open kinematic chain according to one embodiment of the present invention.
Figure 6B:
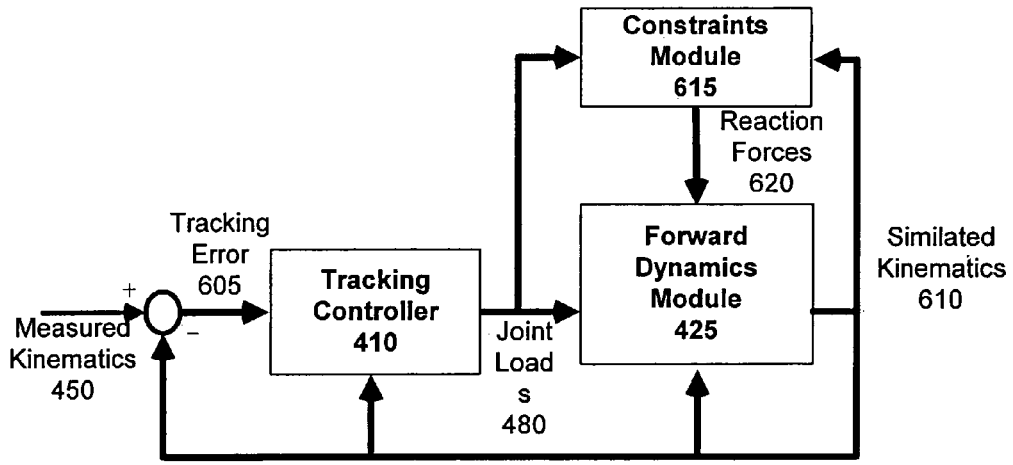
FIG. 6B is a block diagram of a tracking system where a serial chain system is modeled as a closed kinematic chain according to one embodiment of the present invention.

FIGS. 6A and 6B illustrate block diagrams of embodiments of a tracking system when only measured kinematics 450 are available. FIG. 6A illustrates an embodiment where a serial chain system is modeled as an open-kinematic chain, such as the single support phase of gait. For an open chain system, reaction forces and moments need not be estimated or measured for joint load estimation or for prediction of simulated kinematics 610. FIG. 6B illustrates an embodiment when a serial chain system is modeled as a closed kinematic chain, such as the double support phase of gait. Open and closed chain embodiments of the tracking system are described in more detail below. For closed chain systems, reaction forces and moments need to be estimated or measured for joint load estimation or for prediction of simulated kinematics 610. As illustrated in FIG. 6B, constraints module 615 is used to estimate reaction forces 620, which are inputted into forward dynamics module 425. According to one embodiment of the present invention, reaction forces 620 are analytically estimated using the joint load, and previously simulated kinematic data simulated at a previous time. For example, the previously simulated kinematic data is simulated at the previous time-step.

Figure 6C:
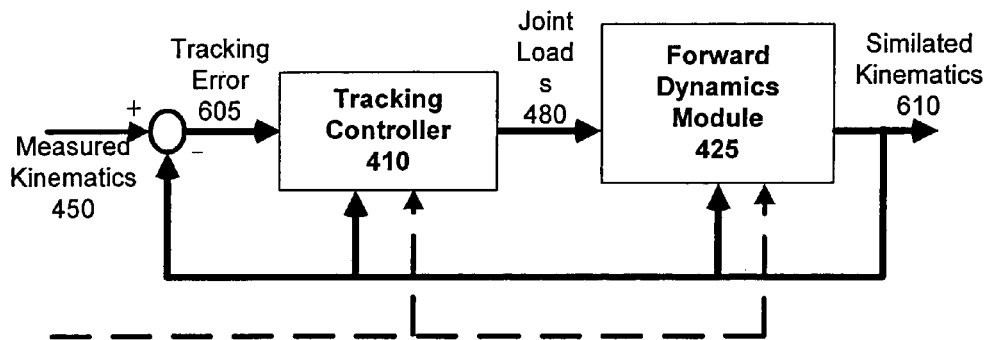
FIG. 6C is a block diagram of a tracking system when kinematic measurements as well as reaction force measurements are available according to one embodiment of the present invention.

FIG. 6C illustrates a block diagram of an embodiment of the tracking system when measured kinematics 450 as well as measured reaction forces and moments 460 are available, which may be obtained, for example, from motion capture and force plate measurements.

The choice between a recursive dynamics method versus a closed form dynamics method depends on the available sensing modality and the specific application. For example, closed form dynamics is well suited for joint load estimation or prediction of simulated kinematics 610 for the tracking system illustrated in FIG. 6B, which involves a closed chain system with only measured kinematics 450 available. On the other hand, the recursive dynamics method is less sensitive to parametric uncertainties in a serial chain system. The recursive dynamics method is well suited for joint load estimation or prediction of simulated kinematics 610 for the tracking systems illustrated in FIG. 6C, which involves an open or closed chain system with both measured or estimated kinematics as well as reaction forces and moments 460 available.

III. Closed Form Dynamics Embodiments

Various embodiments of the present invention express the equations of motion in closed form. For example, closed form embodiments are useful for analysis of an open or closed kinematic chain with only motion capture data available as an input. Derivation of the closed form dynamic equations for the purpose of tracking control are well studied in the robotics literature and one skilled in the art will recognize that those equations can readily be applied for human motion analysis and synthesis according to the tracking system of the present invention. Examples of derivation of closed form dynamics include Newtonian Mechanics, Lagrangian Formulation, Kane's method, Hamiltonian method. Closed form embodiments include open kinematic chains as well as closed kinematic chains.

A. Closed Form Dynamics Embodiments with Open Kinematic Chains

In closed form embodiments modeled as open kinematic chains, a full kinematic description obtained from motion capture is sufficient to estimate or predict joint loads. An open kinematic chain can be modeled in closed form using differential equation 46 below.

$$M(q)\ddot{q}+H(q,\dot{q})\dot{q}+G(q)=U \quad (46)$$

In equation 46, vector q represents the measured coordinates, M is the inertia matrix, H describes the effect of coriolis and centrifugal forces, and G is the vector of gravitational forces. The vector U represents joint loads. Equation 46 and all its component vectors and matrices are described in detail in J. Craig, Introduction to Robotics: Mechanics and Control, $2^{nd}$ Edition, Addison-Wesley (1989), which is incorporated by reference herein in its entirety.

Error Correction Controller

For closed form embodiments modeled as open kinematic chains, the error correction controller is identical to that presented for recursive computations in equation 26, with the exception that the subscript i has been removed, as described in equation 47 below.

$$\ddot{q}^* = a\ddot{q}_m + K_p(q_m-q) + K_v(\dot{q}_m-\dot{q}) \quad (47)$$

Inverse Dynamics Module 420

For closed form embodiments modeled as open kinematic chains, the control law in equation 48 below is used estimate the joint loads that when applied to the system in equation 46 will reproduce the measured kinematics.

$$U=M(q)\ddot{q}^*+H(q,\dot{q})\dot{q}+G(q) \quad (48)$$

Forward Dynamics Module 425

For closed form embodiments modeled as open kinematic chains, the induced acceleration vector is computed using equation 49 below.

$$\ddot{q}=M^{-1}(q)(U-H(q,\dot{q})\dot{q}-G(q)) \quad (49)$$

The closed loop error dynamics of the control law given by equation 48 is identical to those obtained in the recursive formulation.

B. Closed Form Dynamics Embodiments with Closed Kinematic Chains

For closed form embodiments modeled as closed kinematic chains, such as the double support phase of motion, the effect of constraint forces is included in the equations of motion. The equation of motion for closed form embodiments modeled as closed kinematic chains is given by equation 50 below. In equation 50, J is the Jacobian matrix, and F is a constraint force vector.

$$M(q)\ddot{q}+H(q,\dot{q})\dot{q}+G(q)=U+J^T F \quad (50)$$

Inverse Dynamics Module 420

One problem with conventional techniques is that a unique solution to the system of equation 50 does not exist unless the constraint force F can be measured. One embodiment of the present invention provides a technique for determining a control law U by eliminating the term $J^T F$ from equation 50 by null-space projection. Elimination of constraint forces using the null-space projection has been previously used for bipedal control, as described in Jalics, Hemami, and Clymer, A Control Strategy for Terrain Adaptive Bipedal Locomotion, Autonomous Robots, 4: 243-257 (1997), which is incorporated by reference herein in its entirety.

Let N be the null-space of $J^T$. Pre-multiplying equation 50 by N and incorporating the error correction feedback term $\ddot{q}^*$ results in equation 51 below. The term $N J^T F$ is zero because N is orthogonal to $J^T$. The resulting system may be expressed in the form of equation 52 below. The term b is described in equation 53 below.

$$N\{M(q)\ddot{q}^*+H(q,\dot{q})\dot{q}+G(q)\}=NU \quad (51)$$

$$NU=b \quad (52)$$

$$b=N\{M(q)\ddot{q}^*+H(q,\dot{q})\dot{q}+G(q)\} \quad (53)$$

Since N is not a square matrix in general, a pseudo-inverse solution that minimizes the energy cost function is given by equation 54 below. One skilled in the art will be able to obtain other cost functions that use more parameters than energy consumption to determine a movement profile.

$$U=N^T(NN^T)^{-1}b \quad (54)$$

In an alternative embodiment, joint loads U can be described by the product of a moment arm matrix and muscle forces. If muscles are used as actuators, determining the muscle forces may be achieved using a static optimization solution as described in the following literature, which is hereby incorporated by reference in its entirety: Crowninshield & Brand, A physiologically based criterion of muscle force prediction in locomotion, Journal of Biomechanics, 14:793-801 (1981); Anderson & Pandy, Static and Dynamic Solutions for Gait are Practically Equivalent, Journal of Biomechanics, 34:153-161 (2001), which are incorporated by reference herein in their entirety.

Forward Dynamics Module 425

For closed form embodiments modeled as closed kinematic chains, one way to compute the induced acceleration is described in equation 55 below.

$$\ddot{q}=M(q)^{-1}(U+J^T F-H(q,\dot{q})\dot{q}-G(q)) \quad (55)$$

The forces of constraint F may be computed as functions of the state and the input U using equation 56 below. See Hemami & Wyman, Modeling and Control of Constrained Dynamic Systems with Application to Biped Locomotion in the Frontal Plane, IEEE Transactions on Automatic Control, 24:526-535 (August 1979), which is incorporated by reference herein in its entirety.

$$F=(JM(q)^{-1}J^T)^{-1}\{-\dot{J}\dot{q}+JM(q)^{-1}(H(q,\dot{q})\dot{q}+G(q)-U)\} \quad (56)$$

Although the embodiment provided in equation 56 assumes a hard constraint, one skilled in the art will recognize that other models of contact, including penalty-based methods, can be used to compute the constraint forces.

IV. Synthesis of Novel Motion

In various embodiments of the present invention, forward dynamics module 420 can be used to predict novel motions. See Anderson & Pandy, Dynamic Optimization of Human Walking, Journal of Biomechanical Engineering, 123:381-390, 2001, which is incorporated by reference herein in its entirety. As described above, inverse dynamics module 420 can be used to estimate joint loads necessary for a serial chain system to follow a desired trajectory. For example, inverse dynamics module 420 can calculate the motor commands necessary to drive a neuromuscular system based on desired trajectory information. Forward dynamics module 425 uses the estimated joint loads to calculate simulated kinematic data, which represents segmental position and velocity data for the serial chain system.

In various embodiments, forward dynamics module 425 may be used to predict the simulated kinematics of a serial chain system based on changing one or more original parameters to modified parameters. In various predictive embodiments, error correction controller 415 computes modified acceleration q̈* using original kinematic data that is based on original parameters, and that represents a normal, learned, measured, or observed trajectory. Inverse dynamics module 420 estimates joint loads U based on the original parameters, and forward dynamics module 425 predicts simulated kinematics data based on modified parameters.

In one embodiment, forward dynamics module 425 may be used to predict the kinematic response resulting from changing segment parameters such as mass, inertia, length or center of mass. In another embodiment, forward dynamics module 425 may be used to predict the kinematic response resulting from surgical alterations, such as transferring a muscle from one insertion point to another. See Piazza & Delp, Three-Dimensional Dynamic Simulation of Total Knee Replacement Motion During a Step-Up Task, Journal of Biomechanical Engineering, 123:589-606, 2001, which is incorporated by reference herein in its entirety. In yet another embodiment, forward dynamics module 425 may be used to predict the kinematic response resulting from loading the system. An example of loading the system is an external load in the form of a backpack attached to one of the segments.

According to one embodiment, FIG. 6A represents a tracking system in which forward dynamics module 425 is used to predict the simulated kinematics 610 for an open chain system with measured kinematics 450 available as input. The tracking system of the present invention does not require reaction forces and moments to be measured or predicted for an open chain system. According to another embodiment, FIG. 6B represents a tracking system in which forward dynamics module 425 is used to predict the simulated kinematics 610 for a closed chain system with measured kinematics 450 available as input. In one embodiment of the system in FIG. 6B, reaction forces and moments 115 (FIG. 1) are predicted for input into forward dynamics module 425. Constraints module 615 uses equation 56 above to predict reaction forces 620 inputted into forward dynamics module 425. Forward dynamics module 425 uses the predicted reaction forces 620 to computed induced acceleration q̈ as described in equation 55 above. Further, forward dynamics module 425 predicts the simulated kinematics 610 for the closed chain system by numerical integration of the induced acceleration q̈.

According to one embodiment of the present invention, novel motion is predicted using an approach of recursive dynamics. According to another embodiment of the present invention in which a serial chain system is modeled as an open kinematic chain as described above with reference to FIG. 6A, novel motion is predicted using an approach of closed form dynamics.

According to yet another embodiment of the present invention in which a serial chain system is modeled as a closed kinematic chain as described above with reference to FIG. 6B, novel motion is predicted using an approach of closed form dynamics. To provide one example of this embodiment, reaction forces 620 are analytically estimated using joint loads 480 and simulated kinematics 610, as described above with reference to equation 56. To provide another example of this embodiment, joint loads 480 are determined using a null-space projection technique, as described above with reference to equations 51 through 54.

V. Simulation of an Open Chain System

Simulations conducted using measured data show the efficacy of the tracking system of an embodiment of the tracking system for estimating joint forces and moments. The simulated motion for experimentally obtained measured data is a cycle of human gait.

Figure 7:
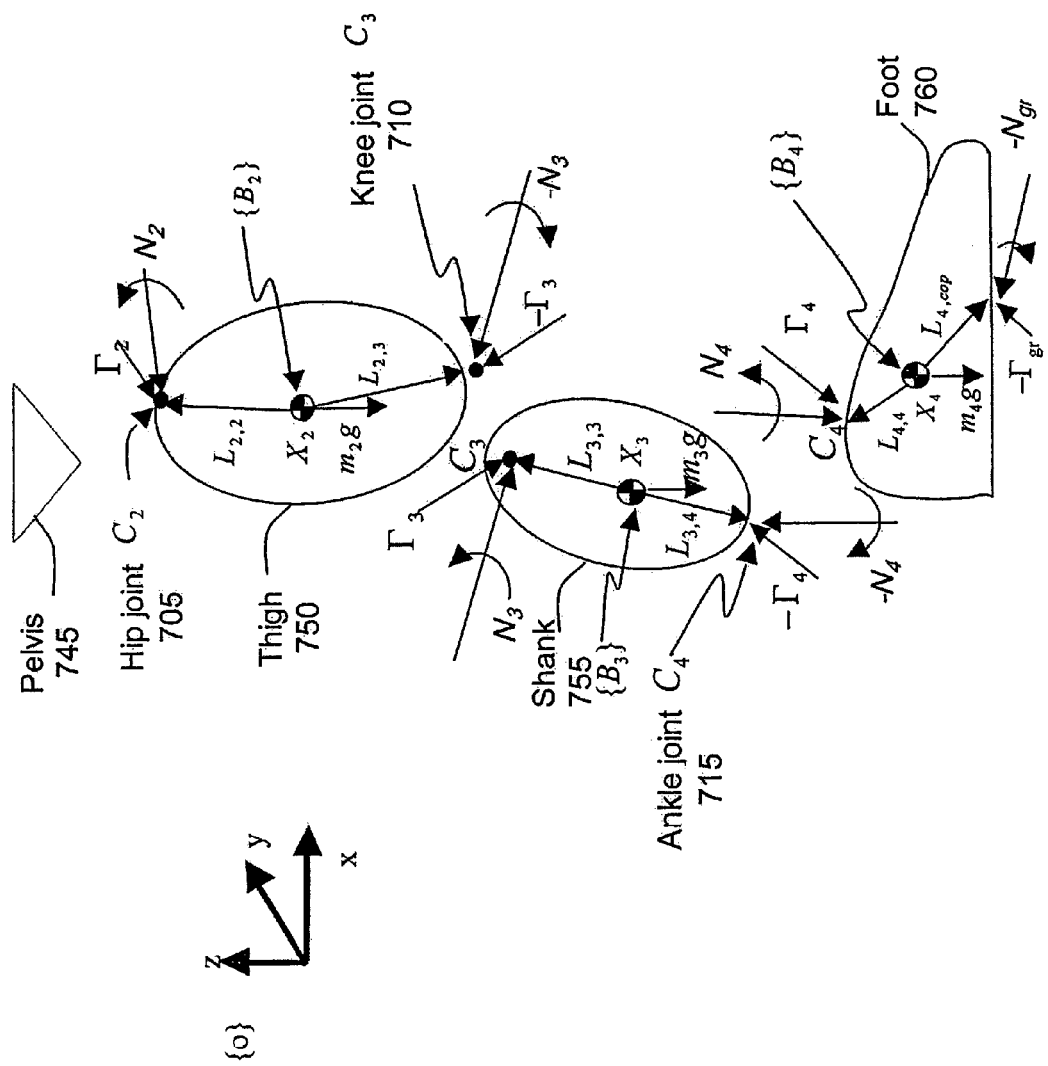
FIG. 7 is a free body diagram illustrating a four segment, three-dimensional lower extremity model that was used in simulations according to one embodiment of the present invention.

FIG. 7 is a free body diagram illustrating a four segment, three-dimensional lower extremity model that was used in the simulations. The four segments include pelvis segment 745, thigh segment 750, shank segment 755 and foot segment 760. Hip joint 705 connects pelvis segment 745 and thigh segment 750. Knee joint 710 connects thigh segment 750 and shank segment 755. Ankle joint 715 connects shank segment 755 and foot segment 760. FIG. 7 depicts the joint loads at hip joint 705, knee joint 710 and ankle joint 715. Further, FIG. 7 depicts segment parameters for thigh segment 750, shank segment 755 and foot segment 760. The variables used to represent joint loads and segment parameters have been described in detail with reference to FIGS. 2 and 3 above. In particular, the ground reaction forces and moments, denoted by $\Gamma_{gr}$ and $N_{gr}$ correspond to the reaction forces and moments acting at the distal end of the last segment in the chain, i.e. at foot segment 760.

A. Experimentally Measured Gait Data

Standard gait measurements including motion capture and force plate data were obtained from Vaughan, Davis and O'Connor, Dynamics of Human Gait, Kiboho Publishers, Cape Town, South Africa, $2^{nd}$ ed., 1999 ("Vaughan"), which is incorporated by reference in its entirety. The recorded motion from a Helen Hayes marker set and a series of anthropometric measurements were used to determine the body segment parameters and joint centers based on the statistical regression equations provided by Vaughan. The Euler angles and center of gravity of each body segment were calculated in order to construct the measured coordinates $q_{m_i}$ for each segment.

Figure 11:
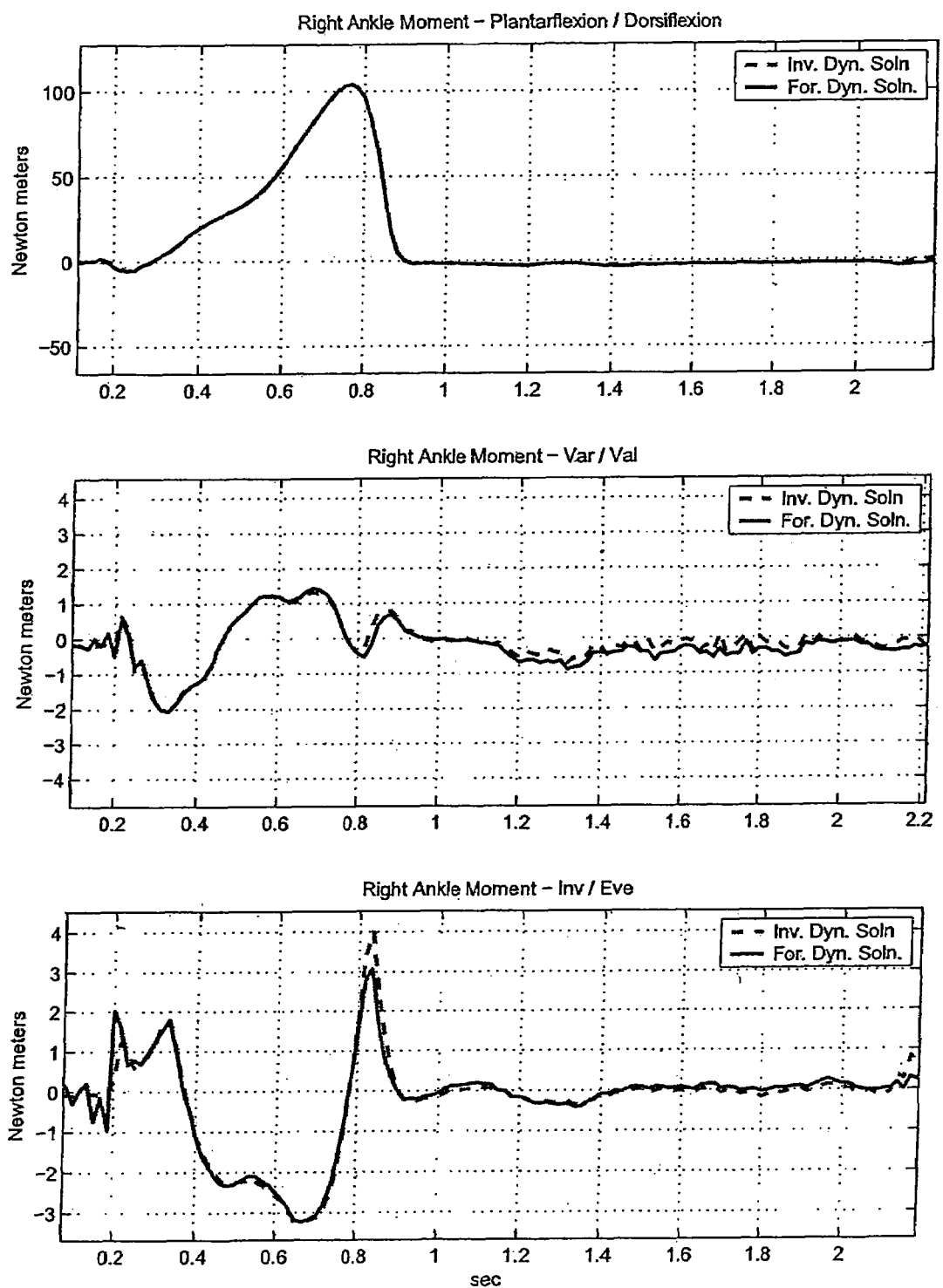
FIG. 11 compares joint moments at an ankle obtained using traditional inverse dynamics analysis to those obtained using a forward dynamics solution according to one embodiment of the present invention.
Figure 12:
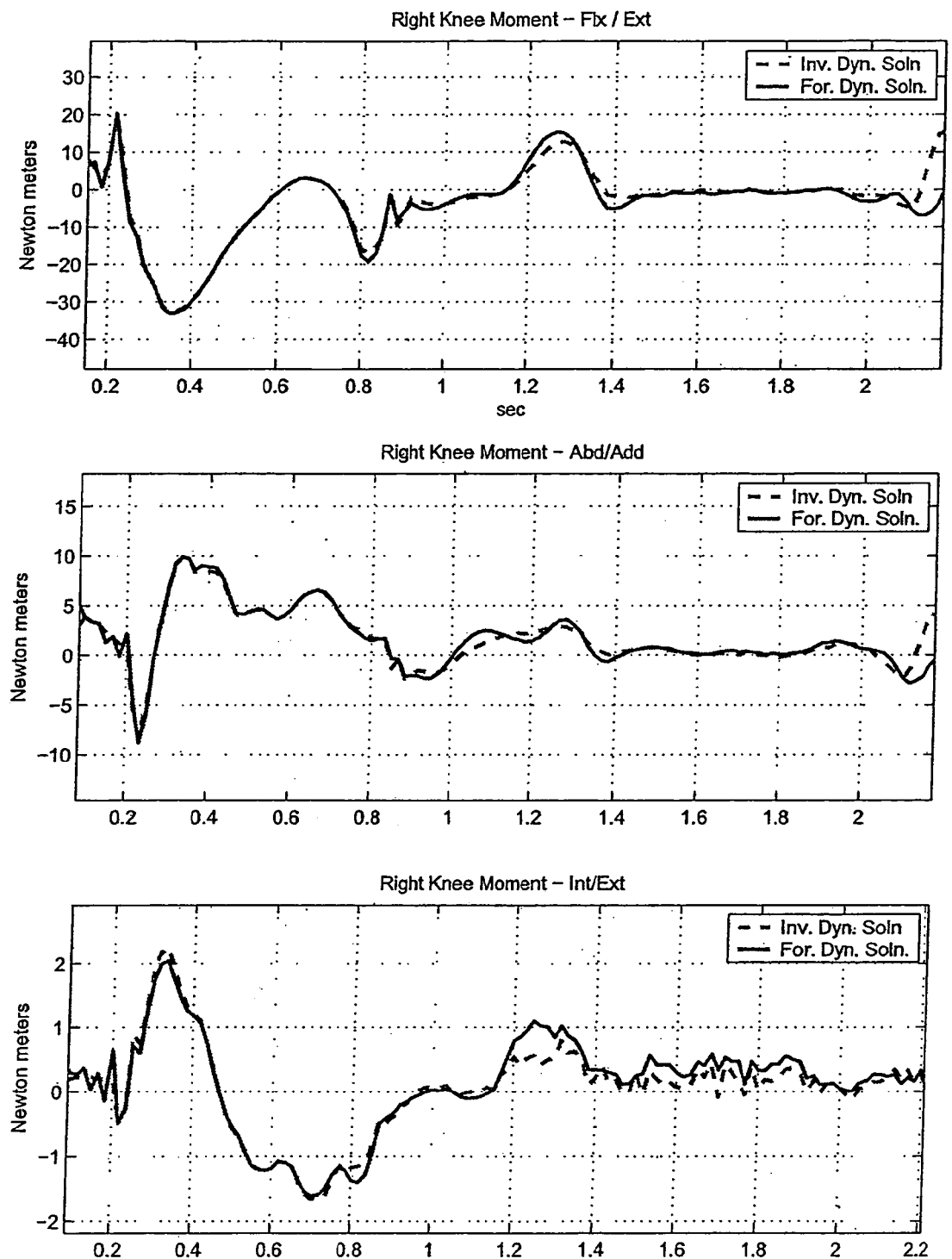
FIG. 12 compares joint moments at a knee obtained using traditional inverse dynamics analysis to those obtained using a forward dynamics solution according to one embodiment of the present invention.
Figure 13:
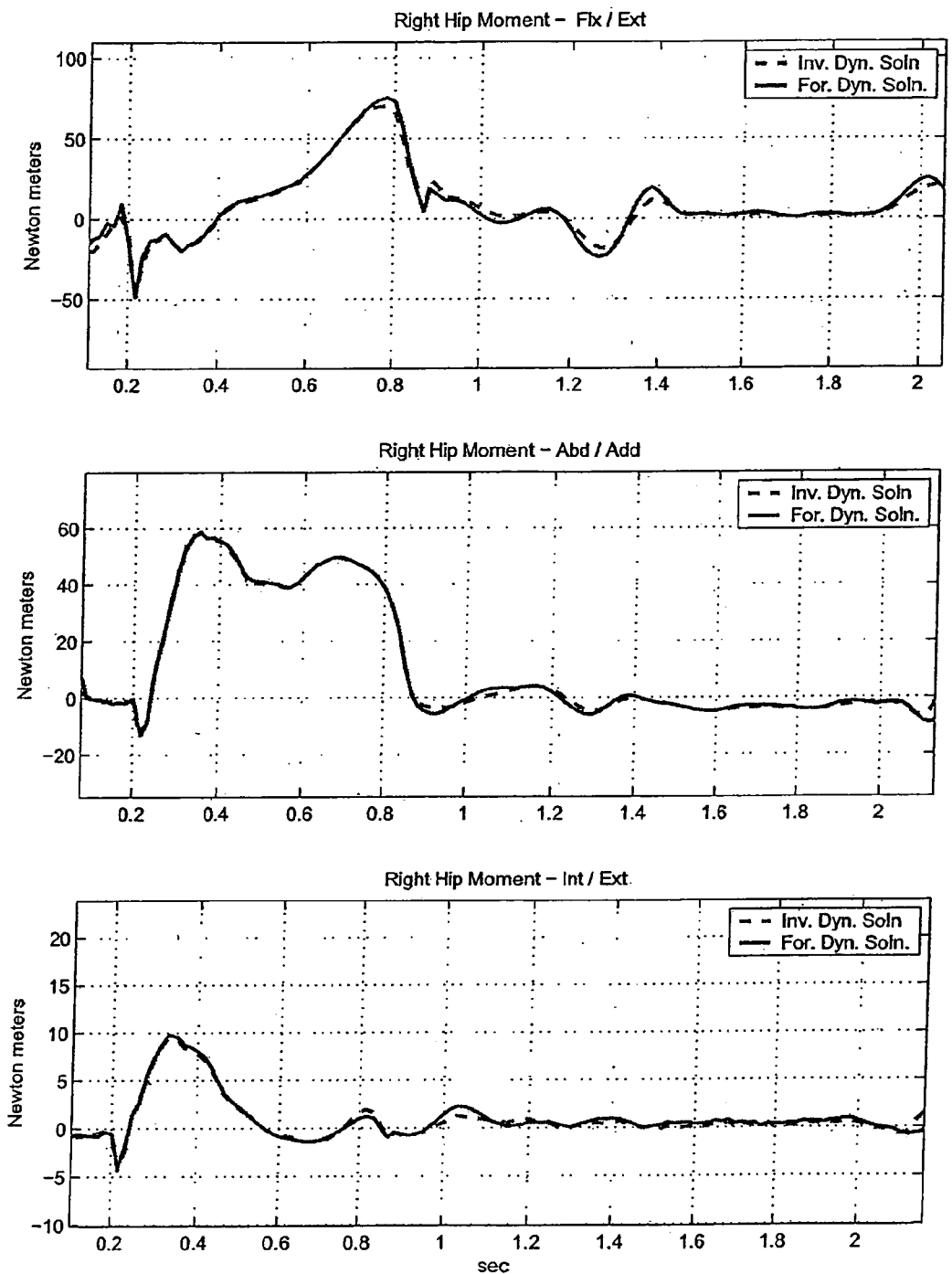
FIG. 13 compares joint moments at a hip obtained using traditional inverse dynamics analysis to those obtained using a forward dynamics solution according to one embodiment of the present invention.

While Euler angles are typically considered in the representation of relative rotational motion between articulating bodies, they do not provide anatomically meaningful description of joint motion. Likewise, joint reaction forces and moments do not convey anatomically meaningful information about the kinetics of motion. The method adopted by Vaughan for human gait analysis was used to display anatomically meaningful kinematics and kinetics. See Grood and Suntay, A Joint Coordinate System for the Clinical Description of Three-Dimensional Motions: Application to the Knee, Journal of Biomechanical Engineering, 105:136-144, 1983, which is incorporated by reference herein in its entirety. The measured Euler angles $\Theta_m$ and simulated Euler angles $\Theta$ were converted to anatomically meaningful joint kinematics shown in FIGS. 8, 9 and 10. Similarly, the joint reaction moments N were converted to anatomically meaningful joint moments as shown in FIGS. 11, 12 and 13.

B. Tracking System Equations for the Lower Extremity System in FIG. 7

The equations for the tracking system FIG. 4 are presented for the lower extremity system considered in FIG. 7.

Inverse Dynamics Module 420

According to one embodiment, inverse dynamics module 420 performs a recursive procedure based on equation 29. The equations required to obtain the force and moment balance estimates starting with joint loads $U_4$ at ankle 715, followed by joint loads $U_3$ at knee 710, and joint loads $U_2$ at hip 705 are described in equation 57 below.

$$U_4 = A_p^{-1}(q_4)\{M_4(q_4)\ddot{q}^*_4 - P_4(q_4, \dot{q}_4) - A_{d_4}(q_4)U_{gr}\}$$

$$U_3 = A_p^{-1}(q_3)\{M_3(q_3)\ddot{q}^*_3 - P_3(q_3, \dot{q}_3) - A_{d_3}(q_3)U_4\}$$

$$U_2 = A_p^{-1}(q_2)\{M_2(q_2)\ddot{q}^*_2 - P_2(q_2, \dot{q}_2) - A_{d_2}(q_2)U_3\} \quad (57)$$

The output of inverse dynamics module 420 is a vector containing the forces and moments at all three joints, represented in equations 58 below.

$$U = [U_2^T U_3^T U_4^T]^T \quad (58)$$

Error Correction Controller 415

From equation 26 above, equations for error correction controller 415 are given by equations 59, 60 and 61 below.

$$\ddot{q}^*_4 = a\ddot{q}_{m_4} + K_{p_4}(q_{m_4} - q_4) + K_{v_4}(\dot{q}_{m_4} - \dot{q}_4) \quad (59)$$

$$\ddot{q}^*_3 = a\ddot{q}_{m_3} + K_{p_3}(q_{m_3} - q_3) + K_{v_3}(\dot{q}_{m_3} - \dot{q}_3) \quad (60)$$

$$\ddot{q}^*_2 = a\ddot{q}_{m_2} + K_{p_2}(q_{m_2} - q_2) + K_{v_2}(\dot{q}_{m_2} - \dot{q}_2) \quad (61)$$

The output of error correction controller 415 is an array represented in equation 62 below.

$$\ddot{q}^* = [\ddot{q}^*_2{}^T \ddot{q}^*_3{}^T \ddot{q}^*_4{}^T]^T \quad (62)$$

Forward Dynamics Module 425

The induced linear and angular acceleration vector for each segment is computed from equation 31 as described in equations 63 below. The induced acceleration array $\ddot{q}^*$ for all three segments is given by equation 64 below.

$$\ddot{q}_4 = M_4^{-1}(q_4)[P_4(q_4, \dot{q}_4) + A_{p_4}(q_4)U_4 + A_{d_4}(q_4)U_{gr}]$$

$$\ddot{q}_3 = M_3^{-1}(q_3)[P_3(q_3, \dot{q}_3) + A_{p_3}(q_3)U_3 + A_{d_3}(q_3)U_4]$$

$$\ddot{q}_2 = M_2^{-1}(q_2)[P_2(q_2, \dot{q}_2) + A_{p_2}(q_2)U_2 + A_{d_2}(q_2)U_3] \quad (63)$$

$$\ddot{q} = [\ddot{q}_2^T \ddot{q}_3^T \ddot{q}_4^T]^T \quad (64)$$

Using well-known techniques of numerical integrations, forward dynamics module 425 numerically integrates induced acceleration array $\ddot{q}^*$ to obtain the vectors q and $\dot{q}$, which are represented in equations 65 below. According to one embodiment, the numerical integration method used for the purpose of the present simulations is a first order Euler method.

$$\dot{q} = [\dot{q}_2^T \dot{q}_3^T \dot{q}_4^T]^T$$

$$q = [q_2^T q_3^T q_4^T]^T \quad (65)$$

The individual matrices in the above equations of motion are described for foot segment 760, shank segment 755 and thigh segment 750 in equations 66, 67 and 68 below.

Foot Segment 760

$$M_4(q_4) = \begin{bmatrix} m_4 \bar{I} & \emptyset \\ \emptyset & I_4 H_4 \end{bmatrix} \quad (66)$$

$$P_4(q_4, \dot{q}_4) = \begin{bmatrix} -m_4 g \\ -I_4 \dot{H}_4 \dot{q}_4 - f(W_4) \end{bmatrix}$$

$$A_{d_4}(q_4) = \begin{bmatrix} -\bar{I} & \emptyset \\ -{}^4R_o \tilde{L}_{4,cop} & -{}^4R_o \end{bmatrix}$$

$$A_{p_4}(q_4) = \begin{bmatrix} \bar{I} & \emptyset \\ {}^4R_o \tilde{L}_{4,4} & {}^4R_o \end{bmatrix}$$

$$U_4 = \begin{bmatrix} {}^o\Gamma_4 \\ {}^oN_4 \end{bmatrix}$$

$$U_{gr} = \begin{bmatrix} {}^o\Gamma_{gr} \\ {}^oN_{gr} \end{bmatrix}$$

Shank Segment 755

$$M_3(q_3) = \begin{bmatrix} m_3 \bar{I} & \emptyset \\ \emptyset & I_3 H_3 \end{bmatrix} \quad (67)$$

$$P_3(q_3, \dot{q}_3) = \begin{bmatrix} -m_3 g \\ -I_3 \dot{H}_3 \dot{q}_3 - f(W_3) \end{bmatrix}$$

$$A_{d_3}(q_3) = \begin{bmatrix} -\bar{I} & \emptyset \\ -{}^3R_o \tilde{L}_{3,4} & -{}^3R_o \end{bmatrix}$$

$$A_{p_3}(q_3) = \begin{bmatrix} \bar{I} & \emptyset \\ {}^3R_o \tilde{L}_{3,3} & {}^3R_o \end{bmatrix}$$

$$U_3 = \begin{bmatrix} {}^o\Gamma_3 \\ {}^oN_3 \end{bmatrix}$$

$$U_4 = \begin{bmatrix} {}^o\Gamma_4 \\ {}^oN_4 \end{bmatrix}$$

Thigh Segment 750

$$M_2(q_2) = \begin{bmatrix} m_2 \bar{I} & \emptyset \\ \emptyset & I_2 H_2 \end{bmatrix} \quad (68)$$

$$P_2(q_2, \dot{q}_2) = \begin{bmatrix} -m_2 g \\ -I_2 \dot{H}_2 \dot{q}_2 - f(W_2) \end{bmatrix}$$

$$A_{d_2}(q_2) = \begin{bmatrix} -\bar{I} & \emptyset \\ -{}^2R_o \tilde{L}_{2,3} & -{}^2R_o \end{bmatrix}$$

$$A_{p_2}(q_2) = \begin{bmatrix} \bar{I} & \emptyset \\ {}^2R_o \tilde{L}_{2,2} & {}^2R_o \end{bmatrix}$$

$$U_2 = \begin{bmatrix} {}^o\Gamma_2 \\ {}^oN_2 \end{bmatrix}$$

$$U_4 = \begin{bmatrix} {}^o\Gamma_3 \\ {}^oN_3 \end{bmatrix}$$

C. Results of Simulations

Figure 8:
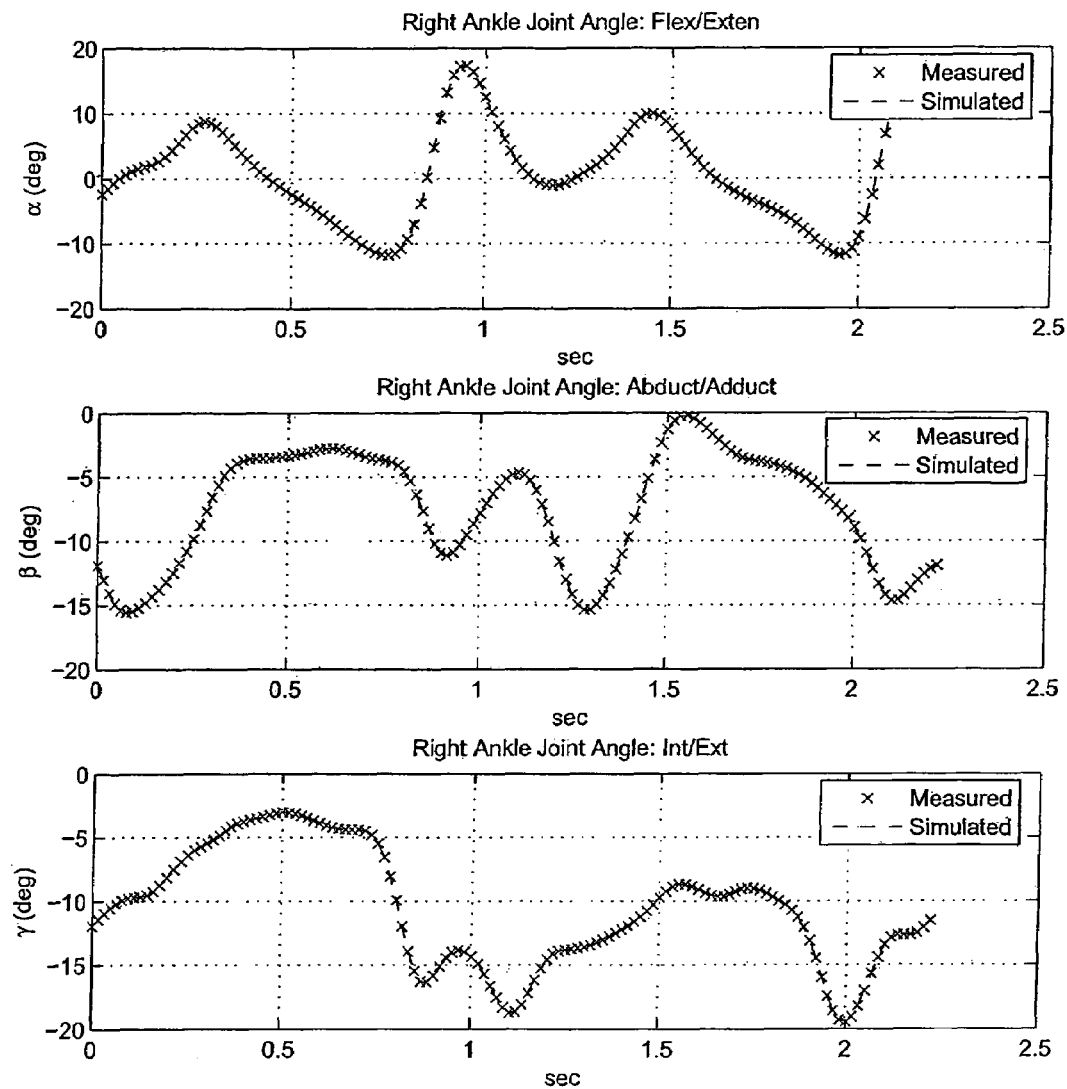
FIG. 8 compares simulated ankle joint angle trajectories versus measured ankle joint angle trajectories for a complete cycle of gait according to one embodiment of the present invention.
Figure 9:
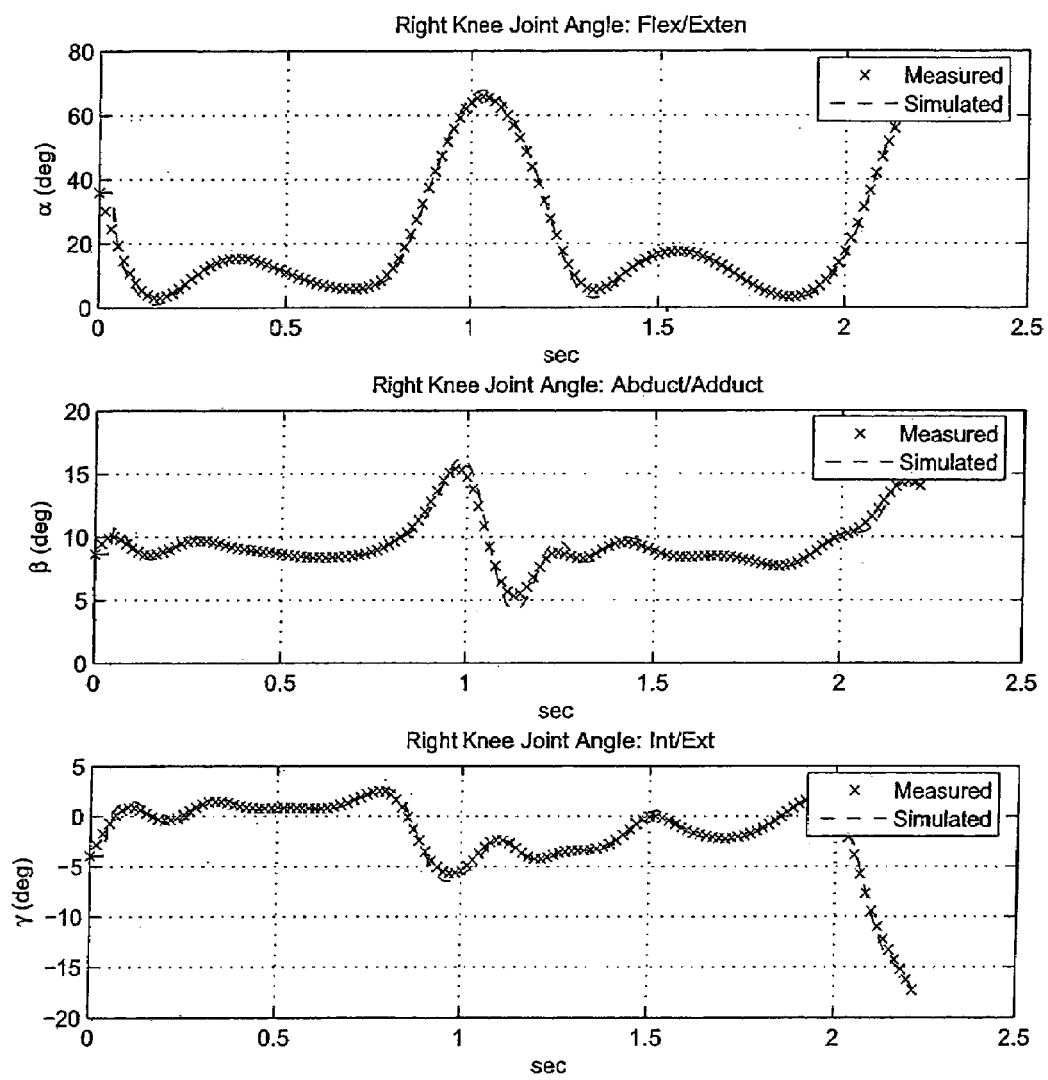
FIG. 9 compares simulated knee joint angle trajectories versus measured knee joint angle trajectories for a complete cycle of gait according to one embodiment of the present invention.
Figure 10:
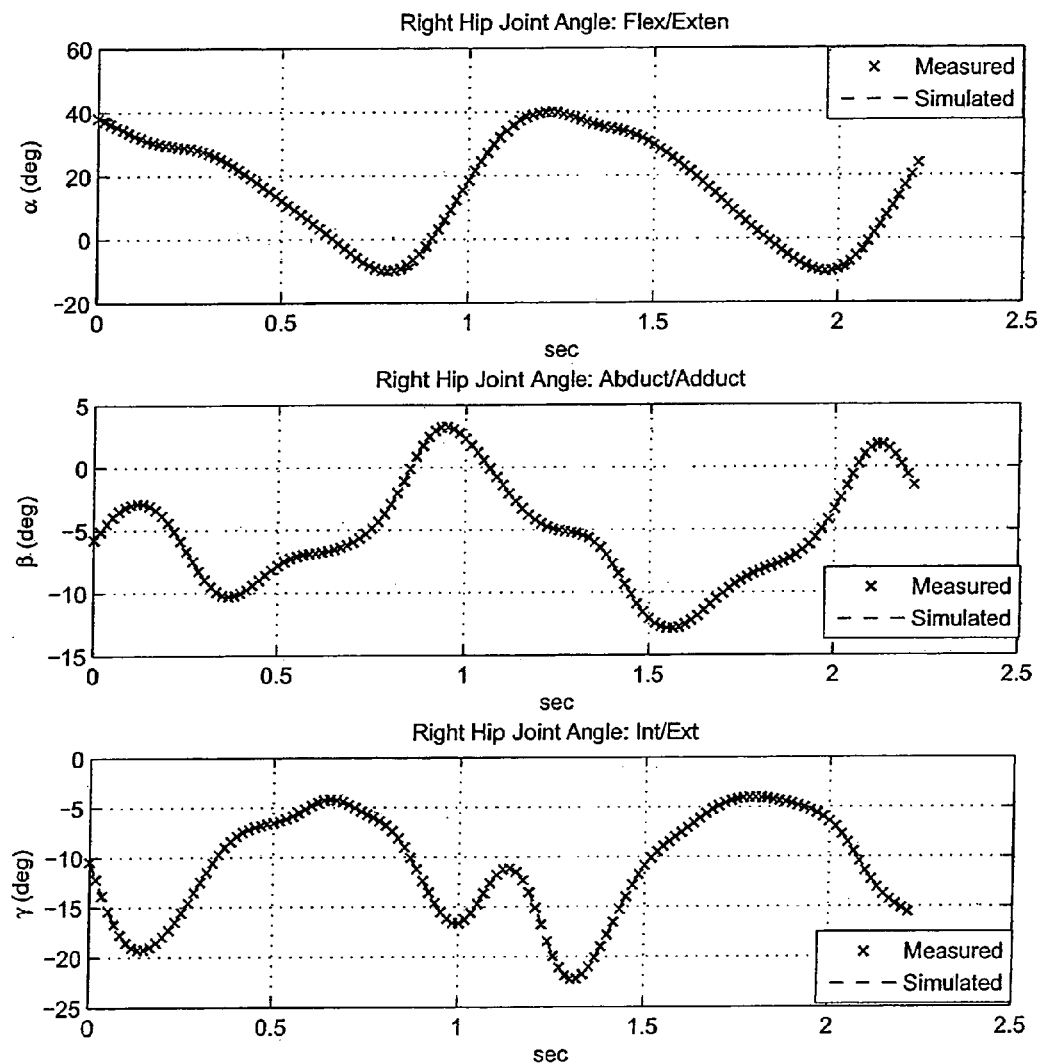
FIG. 10 compares simulated hip joint angle trajectories versus measured hip joint angle trajectories for a complete cycle of gait according to one embodiment of the present invention.

FIGS. 8, 9, and 10 compare simulated joint angle trajectories versus measured joint angle trajectories for a complete cycle of gait according to one embodiment. In these simulations, the position feedback gain of $K_p=4000$ was used and the acceleration terms $\ddot{q}_m$ were omitted in the feedback structure given by Equation 26, i.e. a=0. It is observed that the tracking performance of tracking controller 410 is exceptional in spite of the fact that estimated accelerations $\ddot{q}_m$ were ignored. Various embodiments can further improve the tracking performance by decreasing the sampling rate for numerical integration in forward dynamics module 425 and/or by increasing feedback gains. One skilled in the art will recognize that decreasing the sampling rate requires re-sampling the original signals at a higher frequency. One way to improve tracking performance is by using cubic splines to re-sample the measured kinematic data at a higher frequency. It has been observed that first order numerical integration methods such as Euler's method yield suitable results.

FIGS. 11, 12, and 13 compare the joint moments at ankle joint 715, knee joint 710, and hip joint 705 respectively using traditional inverse dynamics analysis to those obtained using the forward dynamics solution of the present invention. It is observed that if the tracking error is minimized, then the forward dynamics solution will approach the inverse dynamics solution. The forward dynamics solution advantageously avoids the use of accelerations $\ddot{q}_m$ estimated from measured kinematics data. Therefore, in presence of noise, the forward dynamics solution of the present invention will outperform the inverse dynamics solution.

The present invention may be embodied in various forms and should not be construed as limited to the embodiments set forth herein. Rather, these embodiments are provided so that disclosure will be thorough and complete and will fully convey the invention to those skilled in the art. Further, the apparatus and methods described are not limited to rigid bodies.

While particular embodiments and applications of the present invention have been illustrated and described herein, it is to be understood that the invention is not limited to the precise construction and components disclosed herein and that various modifications, changes, and variations may be made in the arrangement, operation, and details of the methods and apparatuses of the present invention without department from the spirit and scope of the invention as it is defined in the appended claims.

What is claimed is:

1. A computer based method of automatically predicting simulated kinematic data for a segment, comprising the steps of:
   determining a modified acceleration using at least original kinematic data, wherein said original kinematic data is based on original parameters;
   estimating a joint load for a joint of the segment using at least said modified acceleration, wherein said joint load is estimated using said original parameters; and
   predicting the simulated kinematic data for the segment based on one or more modified parameters, wherein the simulated kinematic data is predicted using at least said joint load.

2. The method of claim 1, wherein the segment is three-dimensional.

3. The method of claim 1, wherein the segment is two-dimensional.

4. The method of claim 1, wherein said step of determining said modified acceleration includes:
   determining an error value representing a difference between previously simulated kinematic data simulated at a previous time and said original kinematic data; and
   applying a feedback gain to said error value.

5. The method of claim 4, wherein said original kinematic data comprises at least positional kinematic data, said previously simulated kinematic data comprises at least previously simulated positional data, and said error value comprises a positional tracking error representing a difference between said previously simulated positional data and said positional kinematic data.

6. The method of claim 4, wherein said original kinematic data comprises at least velocity kinematic data, said previously simulated kinematic data comprises at least previously simulated velocity data, and said error value comprises a velocity tracking error representing a difference between said previously simulated velocity data and said velocity kinematic data.

7. The method of claim 1, wherein said step of estimating said joint load includes recursively estimating said joint load using one or more successive joint loads at one or more successive joints.

8. The method of claim 1, wherein said step of estimating said joint load uses an approach of closed form dynamics.

9. The method of claim 8, wherein the segment is part of an open kinematic chain.

10. The method of claim 8, wherein the segment is part of a closed kinematic chain.

11. The method of claim 10, wherein a reaction force for said closed kinematic chain is analytically estimated using at least said joint load and previously simulated kinematic data simulated at a previous time.

12. The method of claim 10, wherein said step of estimating said joint load uses a null-space projection technique.

13. The method of claim 1, wherein said step of predicting the simulated kinematic data for the segment further comprises:
   determining an induced acceleration for the segment; and
   determining the simulated kinematic data for the segment by integration of said induced acceleration.

14. A system for predicting simulated kinematic data for a segment, comprising:
   first determining means for determining a modified acceleration using at least original kinematic data, wherein said original kinematic data is based on original parameters;
   means for estimating a joint load for a joint of the segment using at least said modified acceleration, wherein said joint load is estimated using said original parameters; and
   means for predicting the simulated kinematic data for the segment based on one or more modified parameters, wherein the simulated kinematic data is predicted using at least said joint load.

15. The system of claim 14, wherein the segment is three-dimensional.

16. The system of claim 14, wherein the segment is two-dimensional.

17. The system of claim 14, wherein said first determining means for determining said modified acceleration further includes:
   second determining means for determining an error value representing a difference between previously simulated kinematic data simulated at a previous time and said original kinematic data; and
   applying a feedback gain to said error value.

18. The system of claim 14, wherein said means for predicting the simulated kinematic data for the segment further includes:

second determining means for determining an induced acceleration for the segment; and third determining means for determining the simulated kinematic data for the segment by integration of said induced acceleration.

* * * * *